US010010423B2

(12) United States Patent
Kumar

(10) Patent No.: US 10,010,423 B2
(45) Date of Patent: Jul. 3, 2018

(54) ANATOMICAL HUMERAL FIXATION SYSTEM AND METHOD

(71) Applicant: Avinash Kumar, Lakewood Ranch, FL (US)

(72) Inventor: Avinash Kumar, Lakewood Ranch, FL (US)

(*) Notice: Subject to any disclaimer, the term of this patent is extended or adjusted under 35 U.S.C. 154(b) by 0 days.

(21) Appl. No.: 15/389,592

(22) Filed: Dec. 23, 2016

(65) Prior Publication Data

US 2017/0100176 A1 Apr. 13, 2017

Related U.S. Application Data

(63) Continuation-in-part of application No. 14/218,236, filed on Mar. 18, 2014, now Pat. No. 9,526,544.
(Continued)

(51) Int. Cl.
*A61B 17/86* (2006.01)
*A61F 2/40* (2006.01)
(Continued)

(52) U.S. Cl.
CPC .............. *A61F 2/40* (2013.01); *A61B 17/809* (2013.01); *A61B 17/8009* (2013.01);
(Continued)

(58) Field of Classification Search
CPC ..... A61B 17/86; A61B 17/80; A61B 17/8061; A61B 17/8625
See application file for complete search history.

(56) References Cited

U.S. PATENT DOCUMENTS

| 4,463,753 A | 8/1984 | Gustilo |
| 6,162,234 A | 12/2000 | Freedland et al. |

(Continued)

FOREIGN PATENT DOCUMENTS

| CA | 2825282 A1 | 5/2012 |
| CN | 101239002 A | 8/2008 |

(Continued)

OTHER PUBLICATIONS

"Cervical arthrodesis plate / antellor / 2 levels—AnyPlus®—GS Medical," Published: Feb. 6, 2017, URL: http://www.medicalexpo.com/prod/gs-medical/product-103730-746197,html.

*Primary Examiner* — Christopher Beccia
(74) *Attorney, Agent, or Firm* — Dinsmore & Shohl LLP

(57) ABSTRACT

An anatomical shoulder fixation system having a stem having a plurality of holes configured to receive bone screws. The stem having compressible suture locking members protruding from the flared head portion configured to receive and lock an elongated member. The plurality of holes configured to have locking mechanisms abutting the holes. The locking mechanisms preventing the bone screw from backing out while also providing the screw the freedom necessary to realign itself during the healing process. In one locking mechanism embodiment, a locking member utilizing a frustoconical split ring configured lock within a retention groove of the bone screw. Another embodiment has a rotating member with a protrusion that locks into a retention groove of the bone screw. An alternative embodiment has a rotating member that rotates over the bone screw utilizing a complimentary angle between the screw head and the protrusion.

8 Claims, 15 Drawing Sheets

Related U.S. Application Data

(60) Provisional application No. 61/801,675, filed on Mar. 15, 2013.

(51) Int. Cl.
*A61B 17/80* (2006.01)
*A61B 17/82* (2006.01)
*A61B 17/00* (2006.01)
*A61F 2/30* (2006.01)

(52) U.S. Cl.
CPC ...... *A61B 17/8019* (2013.01); *A61B 17/8042* (2013.01); *A61B 17/8047* (2013.01); *A61B 17/8061* (2013.01); *A61B 17/8085* (2013.01); *A61B 17/82* (2013.01); *A61B 2017/00004* (2013.01); *A61F 2002/30034* (2013.01)

(56) References Cited

U.S. PATENT DOCUMENTS

| | | | |
|---|---|---|---|
| 6,599,290 B2 | 7/2003 | Bailey et al. | |
| 6,602,255 B1 | 8/2003 | Campbell et al. | |
| 7,524,325 B2* | 4/2009 | Khalili | A61B 17/7059 606/290 |
| 7,972,336 B2 | 7/2011 | James et al. | |
| 8,211,154 B2 | 7/2012 | Fisher et al. | |
| 8,262,708 B2 | 9/2012 | Michelson | |
| 8,535,313 B1* | 9/2013 | Masson | A61B 17/80 606/232 |
| 8,926,670 B2 | 1/2015 | Jackson | |
| 9,351,774 B2 | 5/2016 | Konieczynski et al. | |
| 2005/0143742 A1 | 6/2005 | Porcher | |
| 2006/0009770 A1 | 1/2006 | Speirs et al. | |
| 2006/0293668 A1* | 12/2006 | May | A61B 17/8605 606/86 A |
| 2007/0118125 A1 | 5/2007 | Orbay et al. | |
| 2007/0123879 A1* | 5/2007 | Songer | A61B 17/8033 606/288 |
| 2007/0213728 A1* | 9/2007 | Lindemann | A61B 17/8042 606/279 |
| 2009/0275947 A1 | 11/2009 | Graham et al. | |
| 2011/0015683 A1 | 1/2011 | Jackson | |
| 2011/0040338 A1 | 2/2011 | Jackson | |
| 2011/0098755 A1 | 4/2011 | Jackson et al. | |
| 2011/0218534 A1 | 9/2011 | Prandi et al. | |
| 2011/0218578 A1 | 9/2011 | Jackson | |
| 2011/0230885 A1 | 9/2011 | Weiner et al. | |
| 2012/0083846 A1 | 4/2012 | Wallenstein et al. | |
| 2012/0209336 A1 | 8/2012 | Jackson et al. | |
| 2013/0046350 A1 | 2/2013 | Jackson et al. | |
| 2013/0090656 A1 | 4/2013 | Huebner et al. | |
| 2013/0178905 A1 | 7/2013 | Graham et al. | |
| 2013/0204300 A1 | 8/2013 | Michelson | |
| 2013/0204306 A1 | 8/2013 | Walker et al. | |
| 2014/0214036 A1 | 7/2014 | Weiner et al. | |
| 2015/0025573 A1 | 1/2015 | Abitbol et al. | |
| 2016/0051290 A1 | 2/2016 | Jackson et al. | |
| 2016/0128746 A1 | 5/2016 | Dunaway | |

FOREIGN PATENT DOCUMENTS

| | | |
|---|---|---|
| CN | 201263715 Y | 7/2009 |
| EP | 2061390 B1 | 3/2016 |
| FR | 2867962 B1 | 5/2007 |
| FR | 3003155 A1 | 9/2014 |
| KR | 100875943 B1 | 12/2008 |
| WO | 2011142828 A1 | 11/2011 |
| WO | 2015051119 A1 | 4/2015 |

* cited by examiner

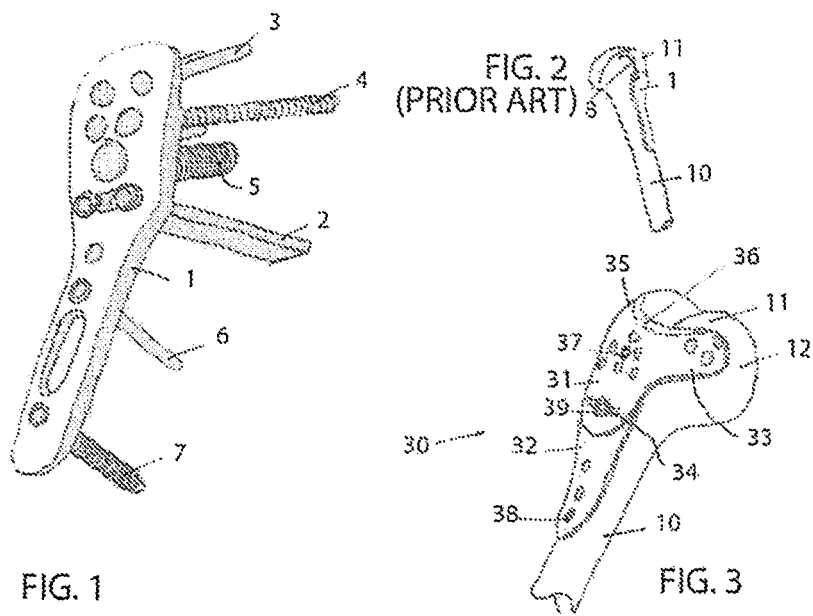

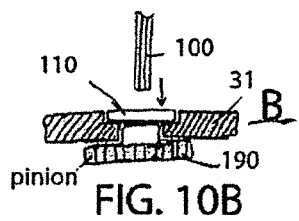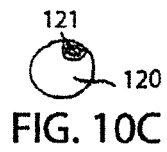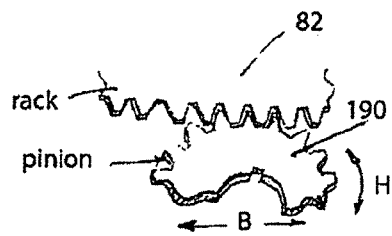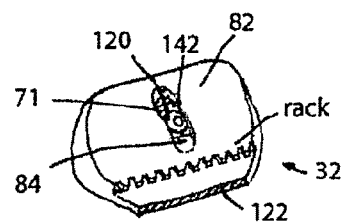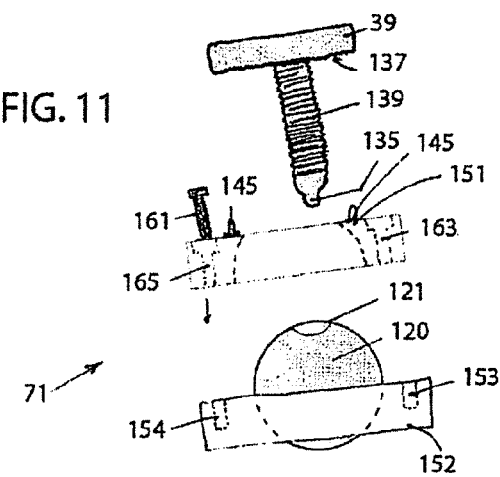

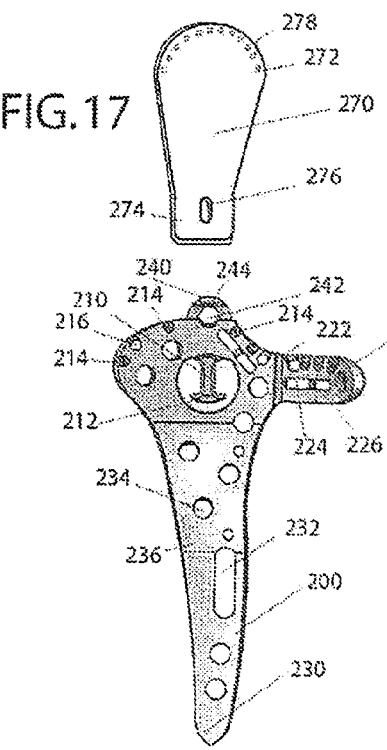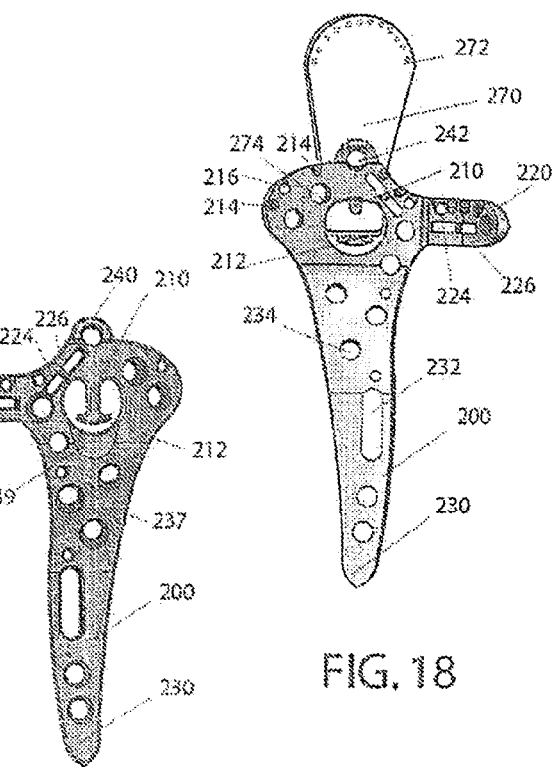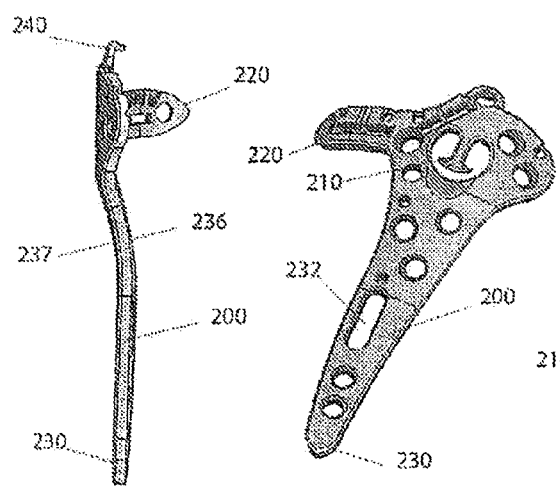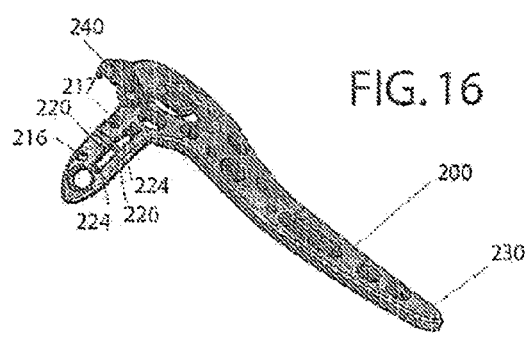
FIG.17
FIG.12
FIG.13
FIG.18
FIG.14
FIG.15
FIG.16

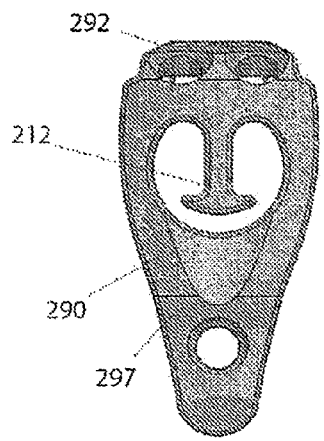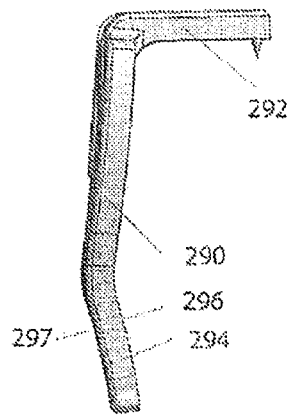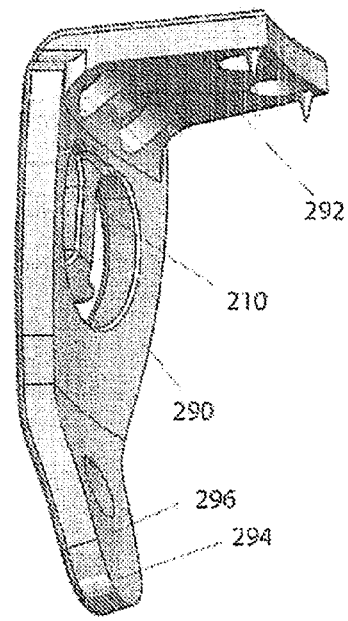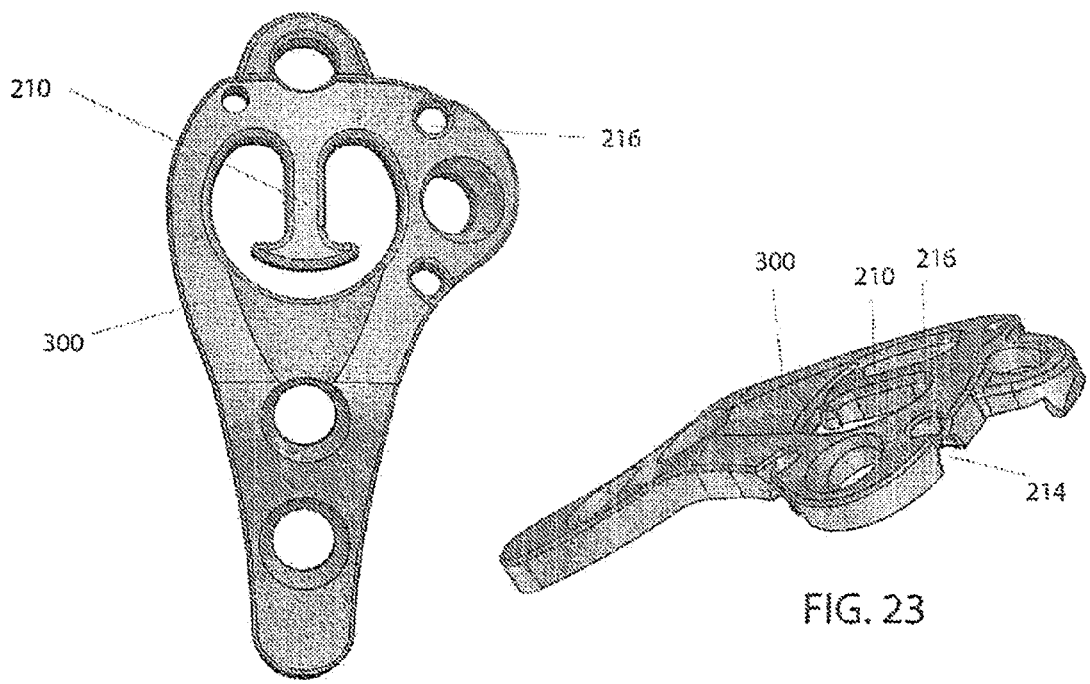
FIG. 19　FIG. 20　FIG. 21　FIG. 22　FIG. 23

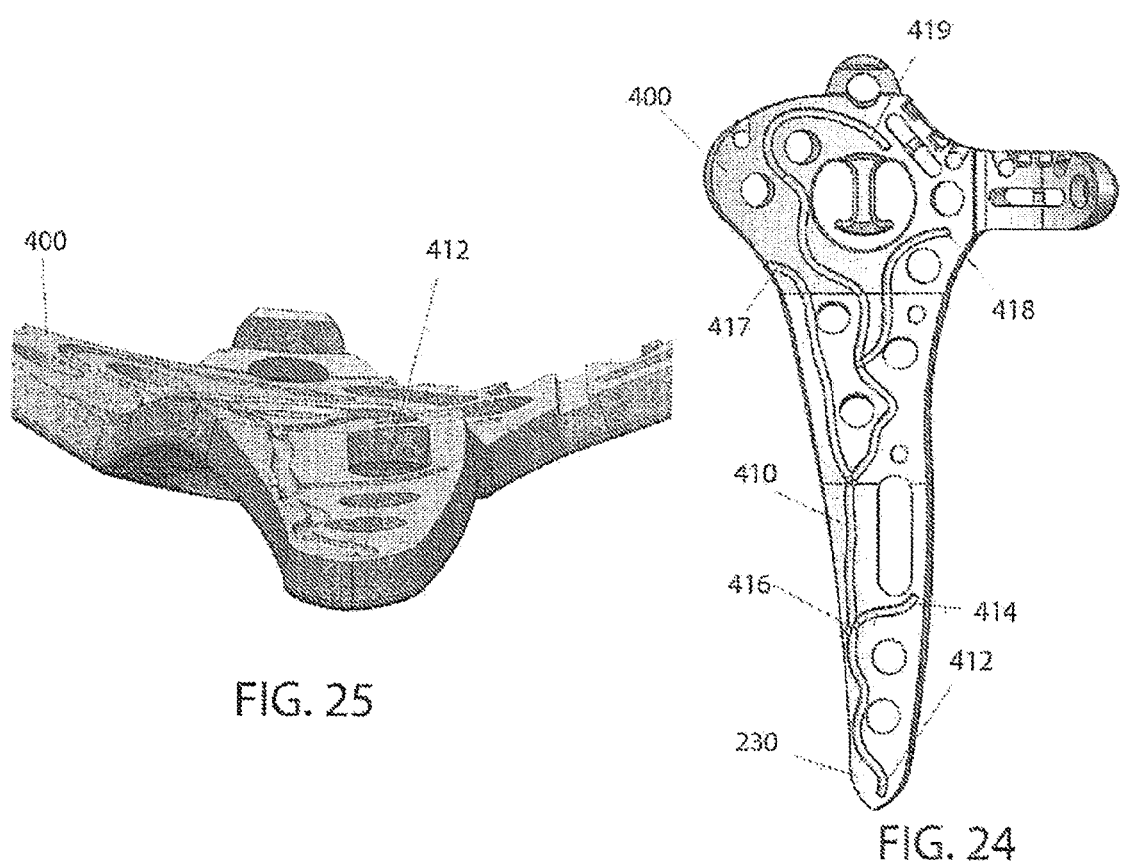

ANATOMICAL HUMERAL FIXATION SYSTEM AND METHOD

CROSS-REFERENCE TO RELATED APPLICATIONS

This application claims priority to the filing date of U.S. patent application Ser. No. 14/218,236, which was filed on Mar. 18, 2014, which in turn claims priority to the filing date of U.S. Provisional Appl. No. 61/801,675, which was filed on Mar. 15, 2013, the specification and drawings of which are hereby incorporated by reference.

FIELD OF THE INVENTION

The field relates to implantable medical devices for orthopedics, especially for shoulder fixation devices and methods

Description of the Related Art

Fixtures for repairing a fracture of a shoulder that using a plurality of screws, pins and the like to fix a fractured shoulder bone are known in the art. For example, U.S. Pat. No. 4,463,753 discloses a bone screw for compressing a fracture. Also, it is known how to make the angle of screws adjustable in a one-piece, solid fixation device, such that the angle of the screws may be adjusted relative to the fixation device. None of the known devices are capable of articulated repositioning of an upper and lower portion of the fixation device.

SUMMARY OF THE INVENTION

An anatomical fixture system and method comprises a lower portion, such as a stem, and an upper portion, such as plate, angled portion or leaf capable of anchoring soft tissues to bone and/or repairing fractures in bone. For example, the anatomical fixture system is used for repairing humeral damage, such as humeral fractures and/or rotator cuff damage caused by torn or severed soft tissues, such as tendons, ligaments and muscles. Screws may be used to fix a lower portion on the bone, and an upper portion may be attached by sutures or screws.

In one example, an anatomical fixation system comprises an upper portion coupled with the greater tuberosity and a lower portion coupled with the lesser tuberosity of the humeral head 11. An arm or wings may be provided. For example the arm or wings may be detachable from the lower portion or the upper portion. A plurality of screws or other fixation devices may be used to secure the lower portion and/or upper portion onto the bone. In one example, a locking mechanism may be provided that adjustably locks the upper portion in relation to the lower portion. For example, the locking mechanism may comprise a bolt capable of coupling the upper portion to the lower portion. For example, the lower portion may be fixed to the bone using one or more screws, and the upper portion may be adjustably coupled to the lower portion by loosely attaching the upper portion to the lower portion with the locking mechanism. Then, the upper portion may be fixed to the humeral head using screws and/or sutures and/or pins as is known in the art.

In one example, the locking mechanism is paired with an adjusting mechanism, such that a fractured head may be repositioned by adjusting the position of the upper portion in relation to the lower portion. Then the locking mechanism may be tightened locking the position of the upper portion in relation to the lower portion of the fixture. The locking mechanism may comprise an element that is bioabsorbable, such that the locking mechanism becomes less effective over time, allowing stress to be accommodated by the anatomical fixture system, initially, and by the bone and soft tissues, eventually, when the bioabsorbable element is partially or fully bioabsorbed. By choosing a bioabsorbable polymer, such as polylactides or other known bioabsorbable polymers, and the dimensions of the bioabsorbable element of the locking mechanism, the system may provide for an extended but not indefinite period for the bone to begin to heal before too much stress is transferred from the system back to the bone. Preferably, the load on the bone and soft tissues is gradually transferred until the bone and soft tissues are healed and become capable of bearing the entire load or a substantial portion of the entire load.

In one example, cut-outs and channels are formed that avoid anatomical features, such as tendons and blood vessels. In one example, a threaded receptacle and a threaded positioner are capable of matingly threading together, such that one portion of the system is angularly displaceable relative to another portion. For example, one portion may be angularly displaced in a plurality of angular directions including arcuately side-to-side and forward-and-back. In one example, the different portions may be translated along a distance and angularly positioned. In yet another example, one portion may be made of a flexible material or a flexible, elastic material capable of freely conforming to anatomical shapes while providing a tensile or tensile elastic stress from a portion where the flexible material is coupled to a rigid fixation system attached to the bone. For example, a lower portion may be a rigid stem fixed to a bone by screws, and a flexible upper portion, such as a leaf, may be coupled to an anchor of the lower portion. The upper portion may be made of a material that readily deforms, such as mesh or patch made of a film or fabric, but the material may be capable of withstanding substantial tensile stresses. In one example, a leaf may be comprised of a film or mesh reinforced by fibers or filaments extending along a length of the material. As is known in the art, such a material may take up substantial tensile stresses without failure, while remaining thin. In one example, such a material comprises a bioabsorbable material capable of being bioabsorbed over time by a human body, when the material is implanted into the body. Such materials are known in the art to include biological tissues and synthetic tissues. A very early bioabsorbable material known in the art is sutures made of cat gut or other such biological tissues. There are many polymers and copolymers capable of being bioabsorbed and the number increases each year.

In one example, a system may be fabricated using 3-D printer technology to provide a custom fit to a patient based on 3-D imaging of the patients humeral bone and imaging of tendons. For example, both the fractured humeral bone and the opposite unfractured humeral bone may be imaged to reconstruct how the system will be formed and adjusted to return the fractured pieces of the humeral bone to a location as close as possible to the anatomical location of the pieces prior to injury. Thus, the system may be anatomically formed to fit the bones and tendons of a particular patients or, alternatively, for a range of patients of similar size and age.

In one example, the fixation system may be positioned further up on the humeral head of the bone, providing significant advantages for angling of the screws that fix the system in place.

In one example, a rack and pinion gear mechanism is provided for repositioning one portion relative to another portion. For example, a slider and a ball may be adjustably engaged for positioning by the rack and pinion gear prior to locking the upper portion in relation to the lower portion with a locking mechanism. Alternatively, an anchor may be provided on a lower portion that engages a portion of an upper portion, such as a leaf, such that the upper portion may be joined to soft tissues, such as tendons, ligaments and muscle, using sutures. For example, the anchor portion may comprise a material taking the shape of an anchor, and the upper portion may comprise a slot capable of being engaged and retained by the anchor, without using any separate locking mechanism. In this example, the anchor and slot prevent the upper portion from being pulled free of the anchor, at least until the portion of the upper portion around the slot is bioabsorbed, for example. In one example, various fixation points (which are not necessarily shaped as an anchor, may be disposed within the lower portion and/or the upper portion of the system. For example, a channel and post extending across a thickness of the channel may be provided, the post providing a location for a suture to be anchored. A post may be formed along an edge comprising through holes through the thickness of one section and surface undercuts extending from an edge to the through holes and forming connecting channels permitting a curved suture needle to extend through the channel and hole to pull a suture through the hole while the section remains fixed to a bone by screws or other fixation devices.

In one example, a greater tuberosity plate is capable of being secured on the greater tuberosity of the humeral bone and comprises a curved inner surface shaped to anatomically fit a humeral head, for example. In another example, a plate comprises an integrally formed extension on one end, angularly extending transversely to a lower portion. For example, the angle may be anatomically arranged at an angle in a range from 40 to 130 degrees to a remaining portion of the integrally formed fixation device. More preferably, the range is 70 to 110 degrees, even more preferably, 80 to 100 degrees. In one example, the extension is perpendicular to another portion of the plate. In another example, a lower portion comprises a stem having an angle corresponding the shape of a humeral bone and humeral greater tuberosity. Typically, the angle is up to 150 degrees with the average humeral neck shaft angle being about 135 degrees.

In another example, a system comprises one or more channels extending into an interior surface. An example is shown of channels in a lower portion of a system, but both the lower and upper portion may have channels. The channels may be used as a way of adjusting the stiffness of portions of the lower and upper portions of the system. For example, a plurality of channels may be formed that intersect at junctions and serve a purpose of adjusting the stiffness of the lower portion, allowing the lower portion to bend in such a way that healing and strength of the bone is improved compared to a strictly rigid lower portion. By allowing some of the stress to be transferred to the bone, channels and bioabsorbable materials may help to provide a more natural callous response during healing.

The system includes locking mechanisms to hold the bone screw from backing out while allowing freedom for reposition of the screw during the healing process. A portion of the bone around the screw may collapse during the healing process as new bone is growing thus pressuring the screw into a different alignment. The locking mechanism prevents the screw from backing out while providing freedom for realignment of the screw during the healing process. A first embodiment of such a locking mechanism is disposed in the top surface of plate's one-piece stem, including the head and/or distal end, in a recessed, circular depression. The depression is abutting to the hole for the bone screw. The locking mechanism has a semi-arcuate shape and is rotated either over the head of the bone screw to lock the seated bone screw into the stem so that the bone screw may not back out or retract, or, in the alternative, the locking mechanism is rotated into to receiving groove within the bone screw to lock the screw into place. The locking mechanism sits flush and/or below the top surface of the plate in both the locked and unlocked position. When unlocked, the locking mechanism does not interfere with the insertion of the bone screw through the bore hole of the plate. In the locking mechanism where the lock is over the bone screw, the bone screw and the locking mechanism each have complimentary angles so that when they overlap the angles match and align with one another. Additionally, the angles provide for the bone screw to be able to have a 2.5 degrees of variation offset from the plate.

In yet another embodiment, the plate's one-piece stem including the head and/or distal end has an axial locking mechanism to hold the bone screw in place thus keeping the plate secured to the bone. The axial locking mechanism contains a frustoconical shaped split ring, a horizontal retention groove in the plate inner perimeter hole to allow the ring to expand and contract as the bone screw is inserted and seated through the hole, and a bone screw containing a retention groove that matches the size of the split ring. The outside diameter of the split ring fits the horizontal groove of the inner perimeter hole of the plate and the ring's inside diameter is configured to fit the bone screw including the bone screw retention groove.

In yet another embodiment, the plate's one-piece stem including the head and/or distal end has at least one suture locking member attached to a peg that is protruding out of the top surface of the plate, away from the bottom surface of the plate. The suture locking members have a bore that is perpendicular on the axis to the peg. The bore may be 90 degrees or may be at different angles to provide access depending on the application. An elongated member may be inserted through a single suture locking member or through multiple suture locking members. After the interstation of the elongated member, any suture locking member may be compressed with a compression tool to collapse the ball and lock the elongated member in place.

It should be appreciated that the one piece stem including the head, arm, or distal portions of the plate may have any combination of the embodiments presented.

BRIEF DESCRIPTION OF THE DRAWINGS

The following drawings are illustrative examples and do not further limit any claims that may eventually issue.

FIG. 1 illustrates a prior art solid fixation device.

FIG. 2 illustrates the prior art fixation device fixed on a humeral one for fixing a fracture in the humeral bone.

FIG. 3 illustrates an example of an anatomical humeral fixation system as used to repair a humeral fracture.

FIG. 4 illustrates another angle of the example of an anatomical humeral fixation system.

FIG. 5 illustrates another angle of an example without the humerus.

FIG. 6 illustrates a cross section through a portion of an anatomical humeral fixation system.

FIG. 7 illustrates an example of a lower portion of the fixation system.

FIG. 8 illustrates another example of a lower portion of the fixation system having recessed portions for accommodating tendons, such as the bicep tendon.

FIGS. 9A illustrates another example having a detachable lesser tuberosity wing and a detachable greater tuberosity wing.

FIGS. 9B illustrates a detachable greater tuberosity wing.

FIGS. 9C illustrates another detachable wing.

FIGS. 10 is a partial view of an adjusting mechanism.

FIGS. 10A is a perspective view of the adjusting mechanism.

FIGS. 10B is a side view of the adjusting mechanism.

FIGS. 10C is a detailed view of a ball with threaded recess.

FIG. 11 illustrates a mechanism for adjusting the angle of the upper portion relative to the lower portion with a plurality of angular degrees of freedom.

FIG. 12 illustrates another example an anatomical humeral fixation system as used to repair a humeral fracture and/or tears to humeral tendon and/or muscle tissues.

FIG. 13 illustrates an opposite view of the system illustrated in FIG. 12.

FIG. 14 illustrates a side view of the system illustrated in FIG. 12.

FIG. 15 illustrates a perspective view of the system illustrated in FIG. 12.

FIG. 16 illustrates another perspective view of the system illustrated in FIG. 12.

FIG. 17 illustrates a flexible upper portion capable of being coupled with the system of the system illustrated in FIG. 12.

FIG. 18 illustrates a flexible upper portion coupled with the system illustrated in FIG. 12.

FIG. 19 illustrates another example of an anatomical humeral fixation system comprising a rotator cuff plate having a portion extending at a transverse angular direction integrally formed with another portion of the system used for fixing the rotator cuff plate to a bone.

FIG. 20 illustrates a side view of the example illustrated in FIG. 19.

FIG. 21 illustrates an enlarged, perspective view of the example illustrated in FIG. 1

FIG. 22 illustrates yet another example of an anatomical humeral fixation system comprising a greater tuberosity plate.

FIG. 23 illustrates a perspective view of the example of FIG. 22.

FIG. 24 illustrates another example of an anatomical humeral fixation system showing channels formed in an interior surface.

FIG. 25 illustrates a partial perspective view of one end of the system showing a depth of a channel and junctions where channels intersect.

When the same reference characters are used, these labels refer to similar parts in the examples illustrated in the drawings.

DETAILED DESCRIPTION OF THE PREFERRED EMBODIMENTS

Figure 26:
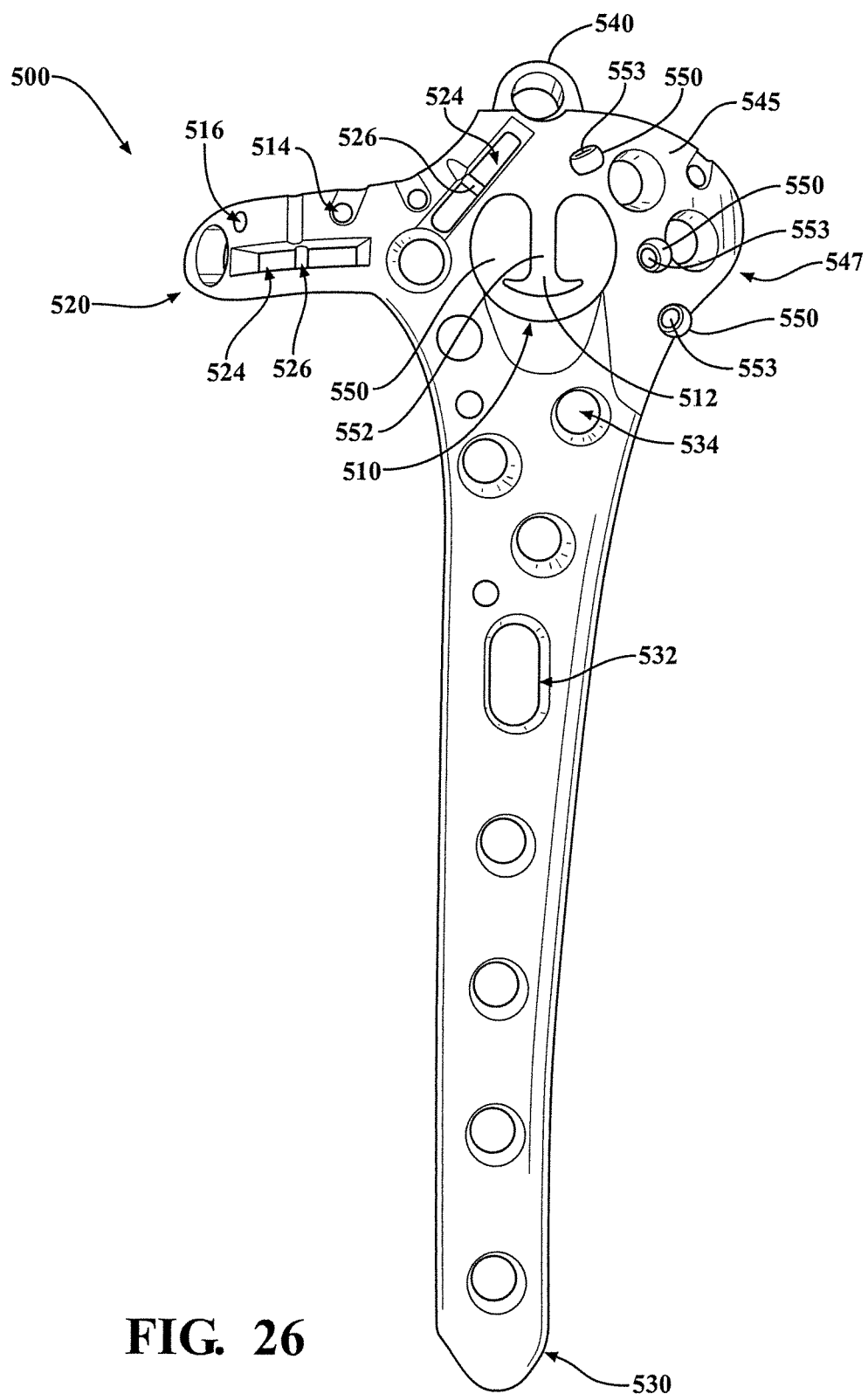
FIG. 26 illustrates another embodiment of the anatomical humeral fixation system.
Figure 27:
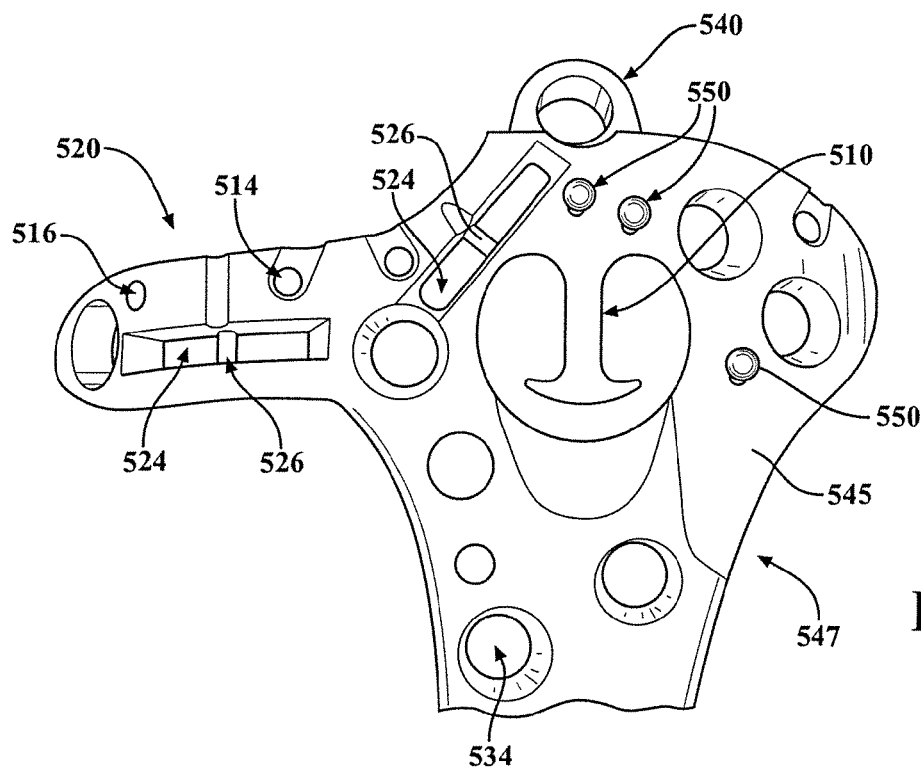
FIG. 27 illustrates a perspective view of the flared head and arm portion illustrated in FIG. 26.
Figure 28:
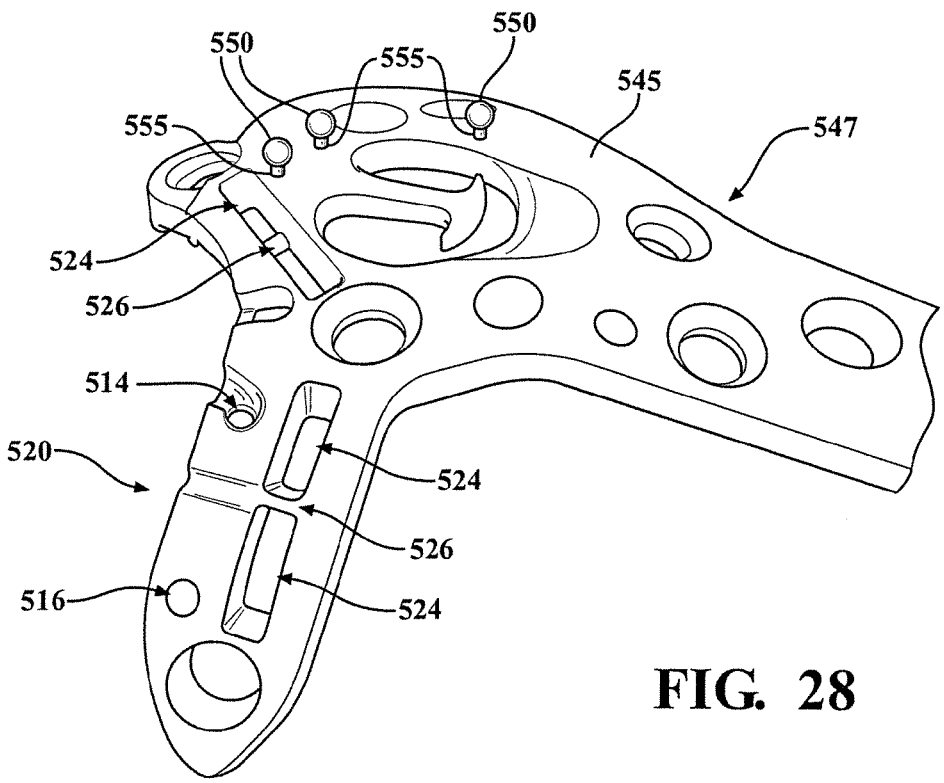
FIG. 28 illustrates another view of the flared head and arm portion illustrated in FIG. 26
Figure 29:
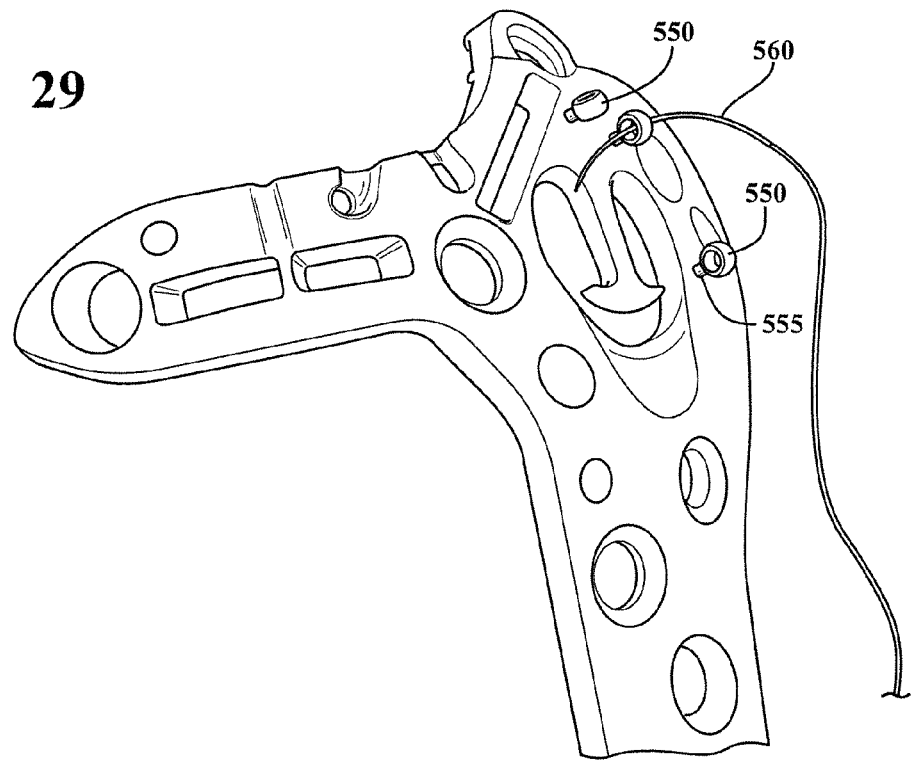
FIG. 29 illustrates the elongated member being inserted through a suture locking member in the in an anatomical humeral fixation system.
Figure 30:
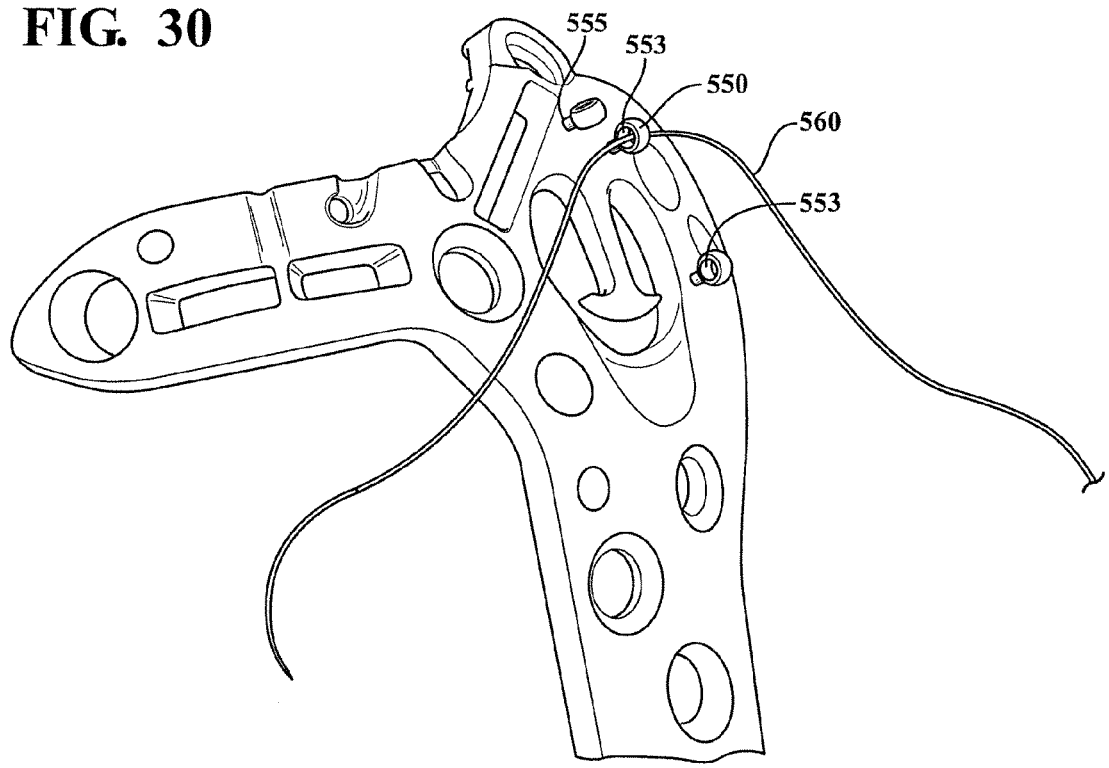
FIG. 30 illustrates the elongated member fully inserted through a suture locking member in an anatomical humeral fixation system.
Figure 31:
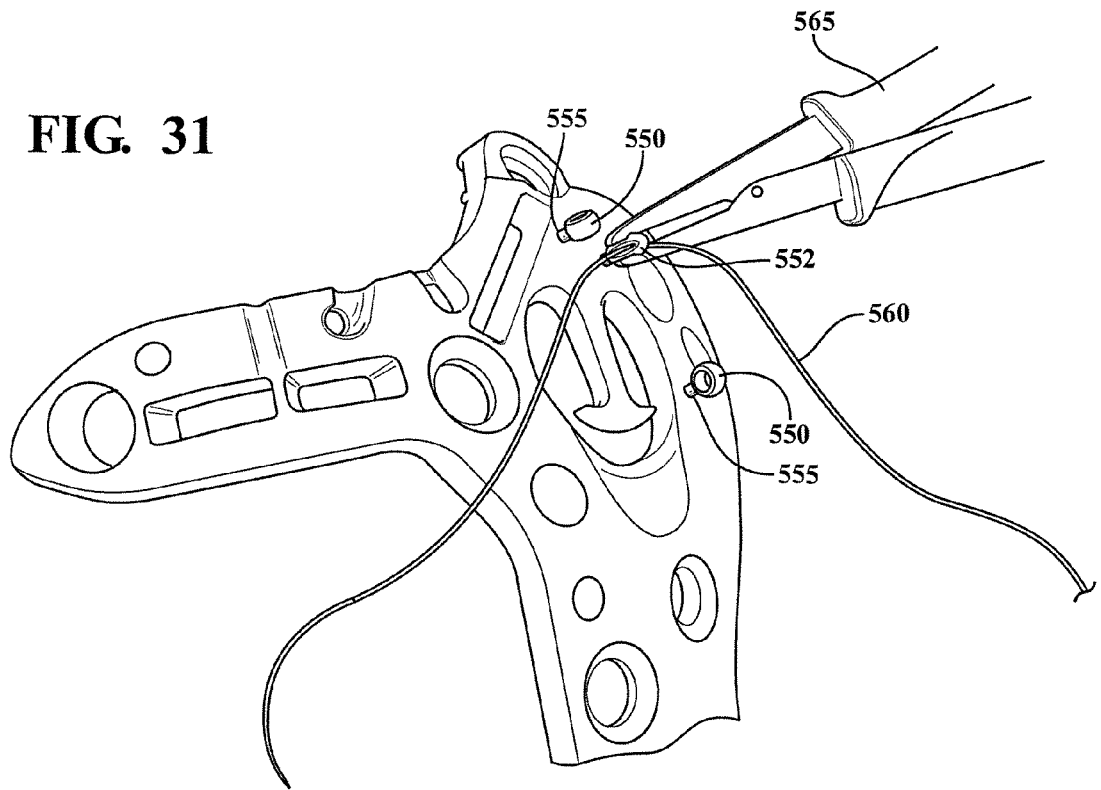
FIG. 31 illustrates the elongated member fully inserted through a suture locking member and the compression tool collapsing the suture locking member in the anatomical humeral fixation system.
Figure 32:
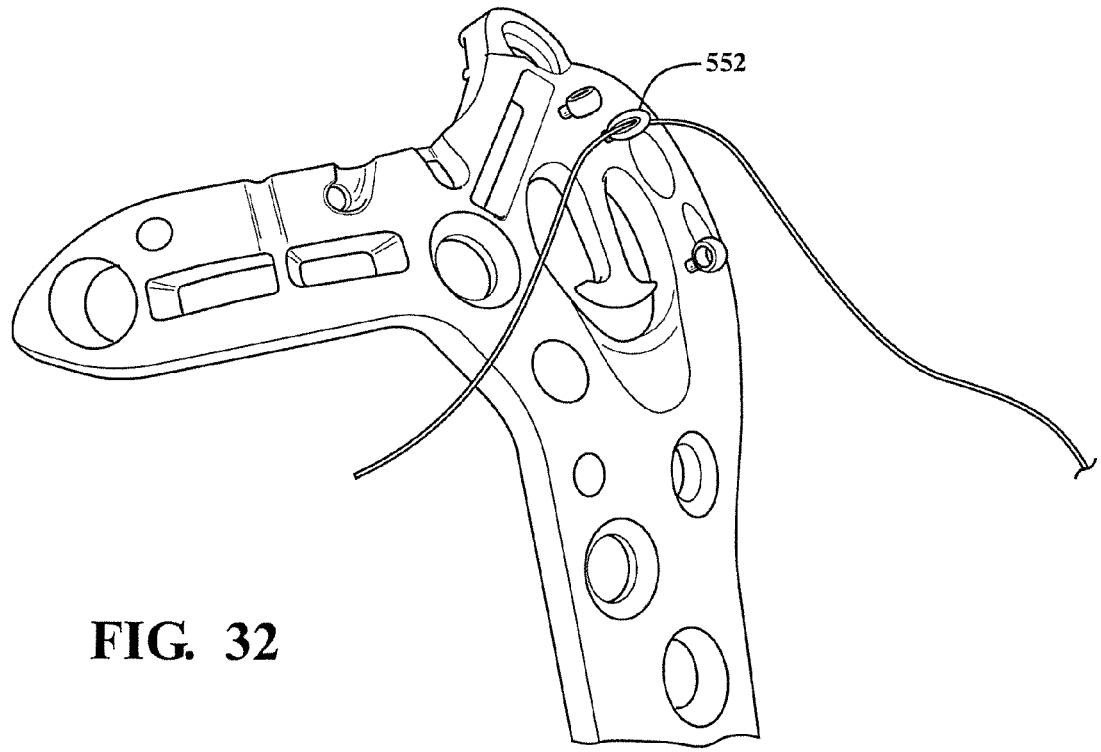
FIG. 32 illustrates the suture locking member fully collapsed in the anatomical humeral fixation system.

The FIG. 1 illustrates a prior art fixation device 1 for a humeral fracture having an optional plate-like pin 2 and screws 4, 5, 6 and pins 3,7 for fixing the fixture onto the humeral bone. FIG. 2 shows how the fixation device is disposed on the humerus. The device 1 must be disposed on the humeral shaft 10 at a location far from the humeral head 11, and sutures 8 must be used to connect tendons and the like to the fixture 1.

In contrast, an anatomical fixture system 30 and method disposes an upper portion 31 in contact with the greater tuberosity 12 and lesser tuberosity of the humeral head 11 using wings 33, 35. A plurality of screws 37 with locking threads may be inserted through the upper portion 31 and into the bone below the fixture, as is known in the art. A locking mechanism 39 may comprise a bolt capable of coupling the upper portion 31 to the lower portion 32. For example, the lower portion 32 may be fixed to the bone using one or more screws 38, and the upper portion may be adjustably coupled to the lower portion by loosely attaching the upper portion 31 to the lower portion 32 with the locking mechanism 39 loosely fit through a slot 34 in the upper portion. Then, the upper portion may be fixed to the humeral head 11 using screws and/or pins as is known in the art. Subsequently, the head 11 may be repositioned by adjusting the position of the upper portion in relation to the lower portion, and then the locking mechanism 39 may be tightened locking the position of the upper portion in relation to the lower portion of the fixture.

In FIG. 4, a cut-out 36 is illustrated that avoids a tendon disposed on the humeral bone 10. In addition, a threaded receptacle 41 and a threaded positioner 42 capable of matingly threading into the receptacle are shown. The positioner 42 is an example of a mechanism for adjusting an angle D of the upper portion 31 in relation to the lower portion 32. FIG. 5 illustrates some of the displacement A, B and angles C,D that are adjustable using the locking mechanism 39 and the adjusting mechanism positioner 42 of the system together with the slot 34.

FIG. 6 illustrates a cross section along line B of FIG. 5, which together illustrate one example of an adjusting mechanism for adjusting the displacement of the upper portion 31 and the lower portion 32 in an up and down direction A. The locking mechanism 39 in this example is threadingly engaged with a slider 71 that is slidingly engaged in a slot 76. That extends from a slit 74 through at least an upper surface of an engagement portion 82 of the lower portion 32 of the system 30. The slit 74 provides an opening 84 on the surface of the engagement portion 82 of the lower portion 32. FIG. 8 illustrates a recessed portion 86 for the biceps tendon that fits under the anatomically shaped lower surface of the lower portion 32, for example. In one example, the system may be fabricated using 3-D printer technology to provide a custom fit to a patient based on 3-D imaging of the patients humeral bone and imaging of tendons. For example, both the fractured humeral bone and the opposite unfractured humeral bone may be imaged to reconstruct how the system will be formed and adjusted to return the fractured pieces of the humeral bone to a location as close as possible to the anatomical location of the pieces prior to injury. Contact surfaces 73, 75, 79, 89 may be prepared in a way that causes these surface to be locked in place once the locking mechanism 39 is tightened, such as by fitting a tool into a correspondingly shaped recess 72 in the locking mechanism 39.

Thus, the system may be anatomically formed to fit the bones and tendons of a particular patients or, alternatively, for a range of patients of similar size and age. One advantage is that the upper portion may be positioned further up on the humeral head of the bone. This provides significant advantages for angling of the screws that fix the system in place, especially when the wings 33, 35 are used. In one example, as illustrated in FIGS. 9A-9C, for example, the wings 33, 35 are detachable. For example, pins 93, 95 may be used to attach the wings 33, 35, respectively. Alternatively, score lines 91 may be provided that allow the wings to be removed by bending the wings with a removal tool, for example. In one example, the wings may be angularly adjustable in an angular direction F.

In one example, repositioning of the upper portion relative to the lower portion may be assisted by an adjusting mechanism as illustrated in the exploded view of FIGS. 10-10C, for example. A tool 100 may be used to rotate a gear 101 by inserting the tool in a recess in the gear, for example. For example, the gear comprise a pinion capable of engaging a rack for translating the rack in direction B compared to the pinion, which is rotated in direction H, for example. FIG. 10A illustrates a partial view of the lower portion and how a rack may be integrated into the engagement portion 82 of the lower portion 32, for example. The cross section 122 illustrates a recess formed for providing the teeth of the rack, as illustrated. The opening 84 shows the slider 71 and a ball 120 adjustably engaged within the slider 71. A detailed view of an example of a ball 120 shows a threaded recess 121, which may be capable of being threadingly engaged with the locking mechanism 39, for example.

FIG. 11 illustrates an example of a slider 71 that is comprised of a ball 120 contained in a recess between two halves 151, 152 of the slider 71. These two halves may be joined together by fasteners 161, 163, 165, 153, 154 or may be bonded, welded, brazed, fitted, or otherwise joined one to the other. The slider 71 may have a raised surface 145, which may be used as a guide and/or locking mechanism, by extending slightly above the surface of the lower portion 32. The locking mechanism 39 may have a tip 135 capable of orienting the ball 121 for proper threading with the mechanism, for example. The threads 139 may be selected to avoid cross threading and stripping, for example. The underside 137 of the head of the locking mechanism 39 may be provided with a locking surface, such as by providing roughness or surface features capable of locking the underside to a corresponding contact surface.

The features illustrated in the drawings may be combined and modified to provide for angular and translational displacement of the upper portion in relation to the lower portion of the system giving many degrees of freedom in repositioning the fractured pieces of bone. For example, a rack and pinion gear may be provided to create compression on a fracture in bone during repositioning of the portions of the system, such as up and down direction A, for example. Alternatively, a set screw 68 or other mechanism may be used to adjust the position of the slider in the slit illustrated in FIG. 6. Various combinations of the illustrated features are within the scope of the inventions disclosed.

FIGS. 12-18 illustrate another example of an anatomical humeral fixation system as used to repair a humeral fracture and/or tears to humeral tendon and/or muscle tissues. The an anatomical humeral fixation system 200 of FIG. 12 may be used to repair a humeral fracture and/or tears to humeral tendon and/or muscle tissues. An one-piece, integrated structure is shown comprising a stem 230, an anchor portion 210 and eyelet 240 and an arm 220. In the example, the stem comprises a narrow distal end, a widening mid-portion and a flared head portion. Various holes 234 and slots 232 extend through the thickness of the stem 230. The anchor portion 210 is formed within an aperture 250 of the flared head portion of the stem 230. The anchor portion 210 comprises an anchor 212 having an elongated portion 252. The illustration of FIG. 12 shows an inner surface 236 that faces a bone 10, when the system is secured to the bone 10 by screws 4, 5, 6 or other fixation devices, as known in. the art. Various fixation points are located within the stem 230 or the arm 220 extending outwardly from the stem 230. For example, a channel 224 and post 226 may be utilized as a suture anchor, or a post may be formed along an edge by holes 216 and surface undercuts 214 forming connecting channels permitting a curved suture needle to fit under the head portion, even when the stem 230 is already fixed to a bone 10 using screws 3, 4, 5. The arm portion. 220 may be made detachable from the stem 230 by providing a score line 222 or other weakness that results in a breakaway arm.

The opposite surface 237 of the stem is illustrated in FIG. 13. A recessed portion 239 allows an end portion 274 or tongue of a mesh or patch, such as the flexible leaf 270 illustrated in FIGS. 17 and 18, even when the stem 230 is fixed to a bone 10 with screws 4, 5, 6. In the example in FIG. 17, a leaf 270 comprises a hole, slit or slot 276 capable of being fit over the anchor 212 of the anchor portion 210. The leaf 270 of FIG. 17 comprises an end portion 274 with a slot 276 and a flared end 272 having holes 278 punched or formed within the flared end 272. FIG. 18 illustrates an example of how the leaf 270 is coupled with the anchor portion 210, 212 of the stem 230. The arm portion 210 has a curvature, as best shown in FIGS. 15 and 16, such that the arm portion 220 anatomically fits a portion of the humeral bone 10. Also, the stem 230 has a curvature such that the stem 230 anatomically fits a portion of the humeral bone 10, as best shown in FIG. 14.

FIGS. 19-21 illustrate another example of an anatomical humeral fixation system comprising a rotator cuff plate 290 having an angled portion 292 with teeth extending from a lower face of the angled portion 292, and having screw holes at the vertex, on the stem 294 and on the angled portion 292. The angled portion 292 extends substantially transversely, at a transverse angular direction, such as a right angle, and is integrally formed with a stem 294. An outer surface 297 faces away from a bone when fixed on the bone. An inner face 296 has a curved surface anatomically shaped for fitting on and over the top of a humeral head. For example, the plate 290 may be fixed on the humeral head by pulling a torn tendon or other soft tissue over the angled portion 292 and biting the teeth into the greater tuberosity of the humeral head at a soft tissue attachment region. A leaf 270 or other flexible mesh or patch may be attached to the anchor portion 210, 212 of the plate 290, and sutures may be used to couple the flared end 272 to the soft tissue.

In one example, the material of the leaf 270 and/or the stem 230 is made of a bioabsorbable material, such as a polylactate or other bioabsorbably prepared polymer. Alternatively, the leaf 270 may be a mesh having an elasticity or visco-elasticity that takes up some or all of the load on the soft tissue, initially, and takes up less stress over time, as the leaf 270 stretches over time, such as by creep or viscoelastic/visco-plastic flow. In another example, the stem is made of a permanent solid, such as by 3-D printing from a polymer, capable of being shaped according to an image of a patient's bone, such as a CT-scan or other three dimensional scan of a patient's skeletal and soft tissue structures. In one example, the stem 230 is formed, cast or machined of a biocompatible metal, such as a steel or titanium alloy.

In FIG. 22, an anatomical humeral fixation system comprises a greater tuberosity plate 300, capable of being secured on the greater tuberosity of the humeral bone, for example. FIG. 23 shows a perspective view illustrating, together with FIG. 22, some of the same elements of the system illustrated in FIGS. 12-21, and having a curved inner surface shaped to anatomically fit a humeral head, for example.

In another example, FIG. 24 shows a stem 230 comprising channels 410 formed in an interior surface 236 of the stem 230. FIG. 25 illustrates an example of a depth and cross junctions of the channels 410. The channels 410 may have branches 412, 414, 416, 417, 418, 419 extending from junctions 416, for example. For example, the channels 410 may be provided to accommodate anatomical features or may be provided to weaken certain portions of the stem 230 to provide greater deformability or flexibility of the stem 230, such that the stem 230 does not remove all of the stress from a bone. By allowing some of the stress to be transferred to the bone, the channels 410 may help to provide a more natural callous response. If combined with a bioabsorbable material, the channels 410 may provide for an engineered transfer of load from the stem 230 to the bone and soft tissues over time.

Now referring to the anatomical humeral fixation system 500 as illustrated in FIGS. 26-43, the system 500 includes three locking mechanism embodiments 568, 600, 700 to hold two bone screw embodiments 576, 750 from backing out while allowing freedom for reposition of the screw during the healing process. A portion of the bone around the screw 576, 750 may collapse during the healing process as new bone is growing thus pressuring the screw into a different alignment. Each locking mechanism embodiment 568, 600, 700 prevents the corresponding bone screw 576, 750 from backing out while providing freedom for realignment of the screw during the healing process. Each locking mechanism embodiment 568, 600, 750 may be used independently or may be part of another locking mechanism. In other words, the system may include all offset locking mechanisms 600 at one or all bone screw holes 534 or it may include both an offset locking mechanism 600 and an axial locking mechanism 568.

Now referring to FIGS. 26-32, an embodiment of an anatomical humeral fixation system as used to repair a humeral fracture and/or tears to humeral tendon and/or muscle tissues shown in this embodiment includes a suture locking member and a screw locking mechanism. As shown in FIGS. 26-32, the anatomical humeral fixation system 500 has one-piece, integrated structure having a stem 530, an anchor portion 510 and eyelet 540 and an arm 520. The stem 530 generally has a narrow distal end, a widening midportion and a flared head portion. Further, the stem 530 has a top surface 545 and a bottom surface 547. The stem 530 is generally made of a surgical grade rigid metal such as a harder steel or titanium materials. Various holes 534 and slots 532 extend through the thickness of the stem 530. The anchor portion 510 is formed within an aperture 550 of the flared head portion of the stem 530. The anchor portion 510 comprises an anchor 512 having an elongated portion 552. Various fixation points are located within the stem 530 or the arm 520 extending outwardly from the stem 530. For example, a channel 524 and post 526 may be utilized as a suture anchor, or a post may be formed along an edge by holes 516 and surface undercuts 514 forming connecting channels permitting a curved suture needle to fit under the head portion, even when the stem 530 is already fixed to a bone. The arm portion 520 may be made detachable from the stem 530 by providing a score line (not pictured) or other weakness that result in a breakaway arm.

The flared head portion of the stem 530 has at least one suture locking member 550 generally in the shape of a sphere or a ball, and typically having a system of three or more, are attached to a peg 555 that is protruding out of the top surface 545 of the stem 530, away from the bottom surface 547 of the stem 530. The peg 555 can be prefabricated with the stem 530 or may be added to the stem 530. The peg 555 is generally made of similar rigid medical grade metal material similar to the material of the stem 530. The suture locking member 550 is generally made of a softer metal so to be collapsible such as, without limitation, aluminum. The suture locking member 550 can be pressed onto the peg 555. The suture locking members 550 have a bore 553 that extend on an axis is generally perpendicular to an axis of the peg 555. The bore 553 may extend at 90 degrees or may be at different angles to provide access depending on the application. An elongated member 560 such as, a suture or wire, is inserted through a single suture locking member 550 or through multiple suture locking members 550. The elongated member may then inserted, tied, wrapped, or any of the like to the soft tissues, such as tendons, ligaments and muscles. After the interstation of the elongated member 560, any suture locking member 550 may be compressed with a compression tool 565 to collapse bore 553 around the elongated member 560 thereby deforming the suture locking member 550 into an oblong shape 552 thus locking the elongated member 560 in place and in turn helping secure or stabilize soft tissues, such as tendons, ligaments and muscles.

Figure 33:
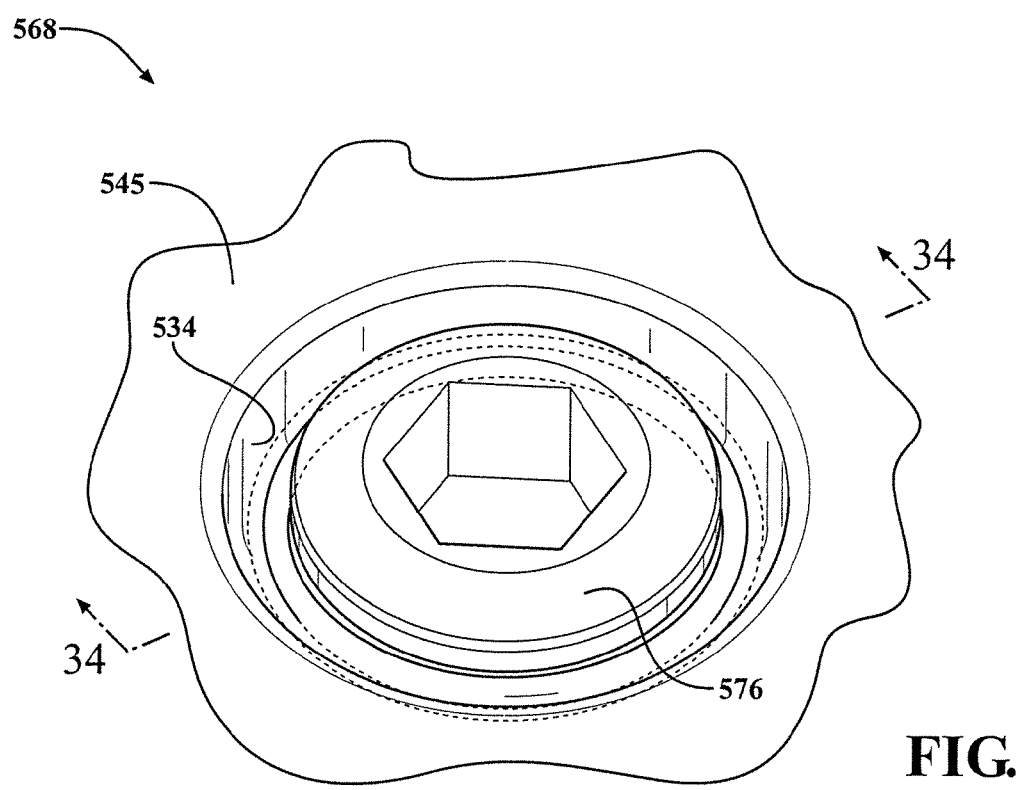
FIG. 33 illustrates a top environmental view of the screw locking mechanism in the locked position.
Figure 34:
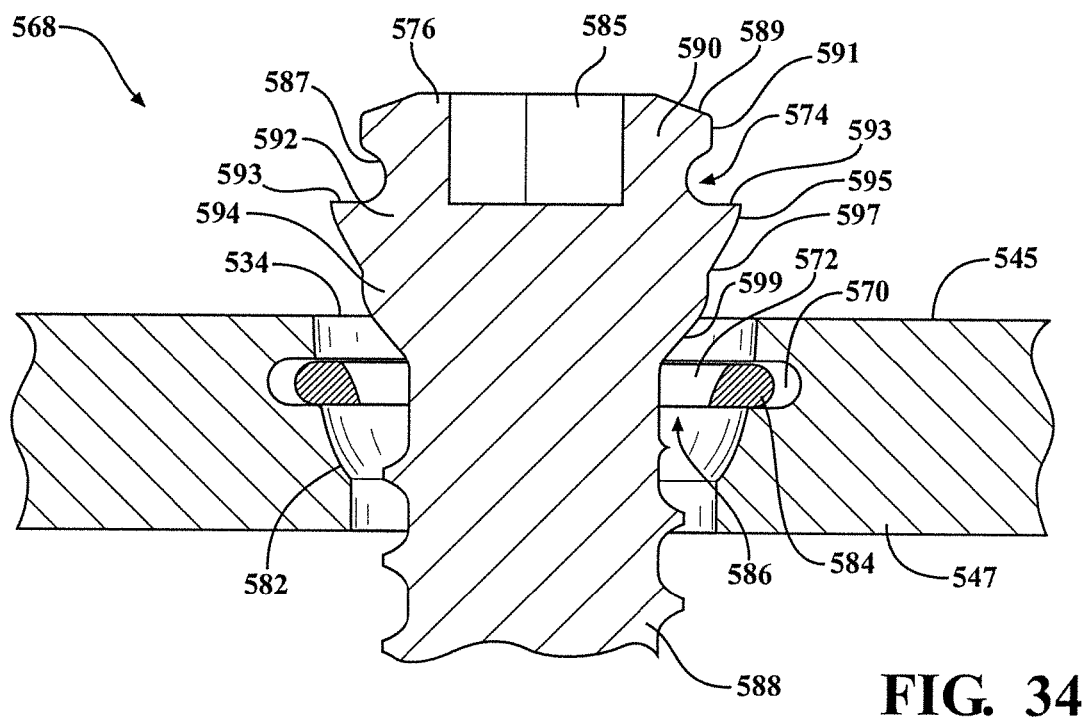
FIG. 34 illustrates a cross section view of the screw locking mechanism of FIG. 33 taken from line 34 showing the bone screw before it is fully seated and locked in the hole of the plate.
Figure 35:
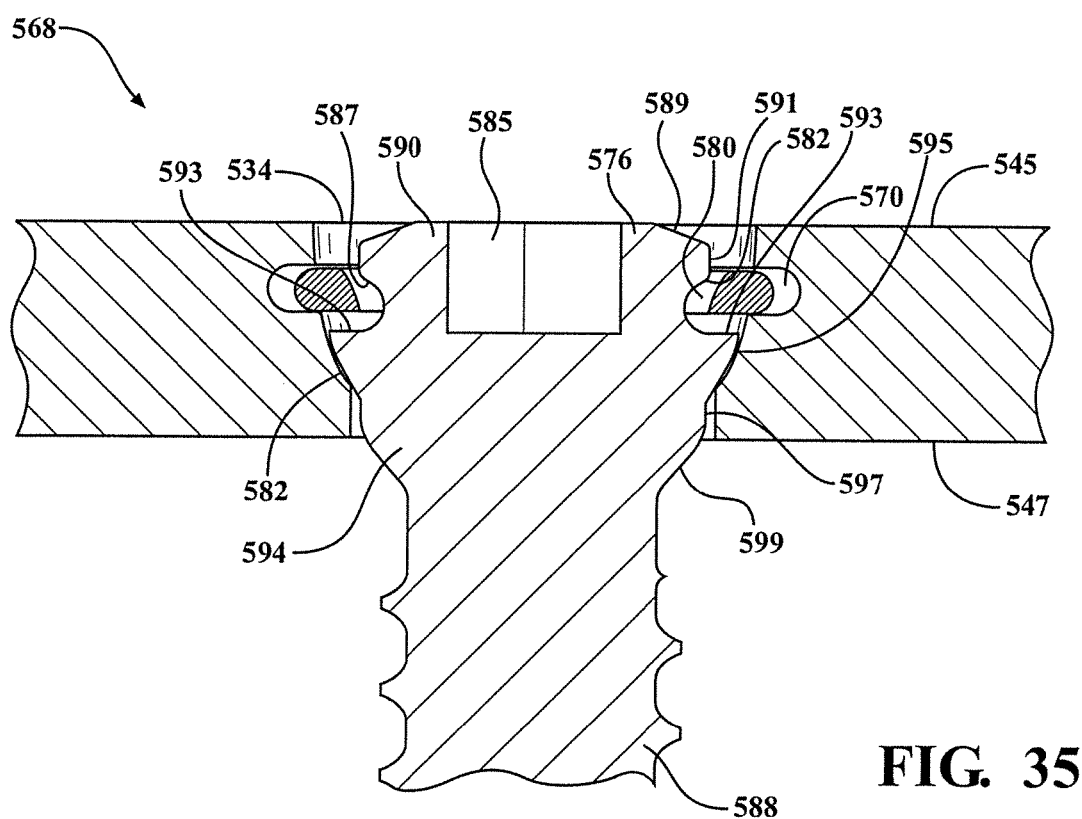
FIG. 35 illustrates a cross section view of the screw locking mechanism of FIG. 33 taken from line 34 showing the bone screw fully seated and locked.
Figure 36:
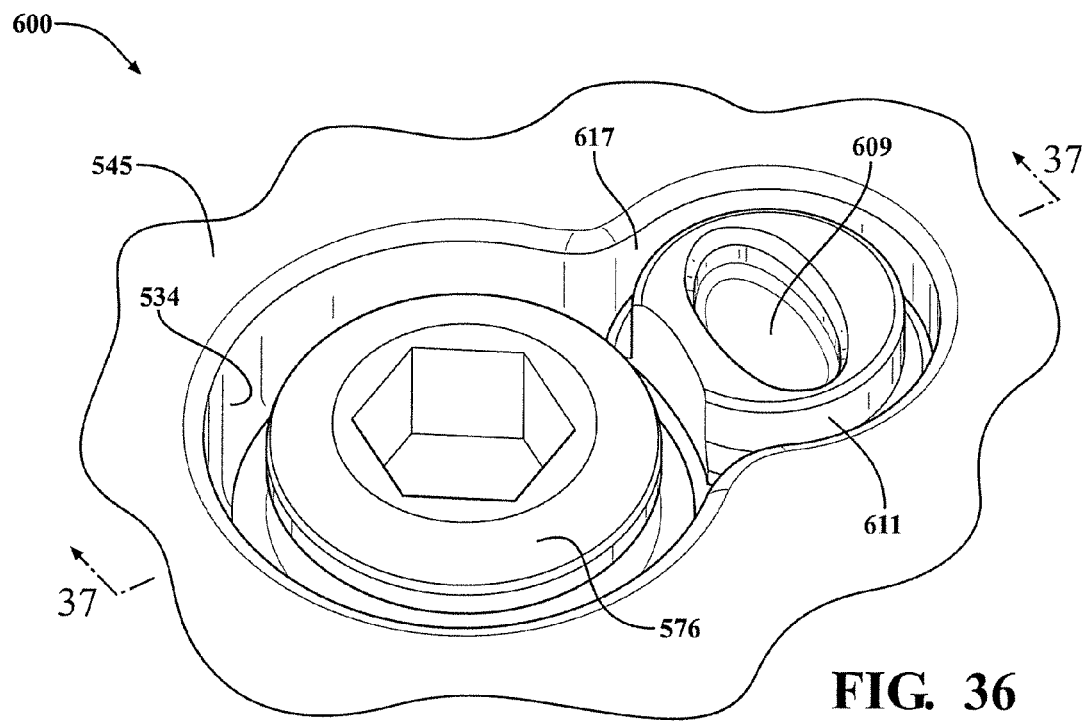
FIG. 36 illustrates a top environment view of the alternative screw locking mechanism in an unlocked position.
Figure 37:
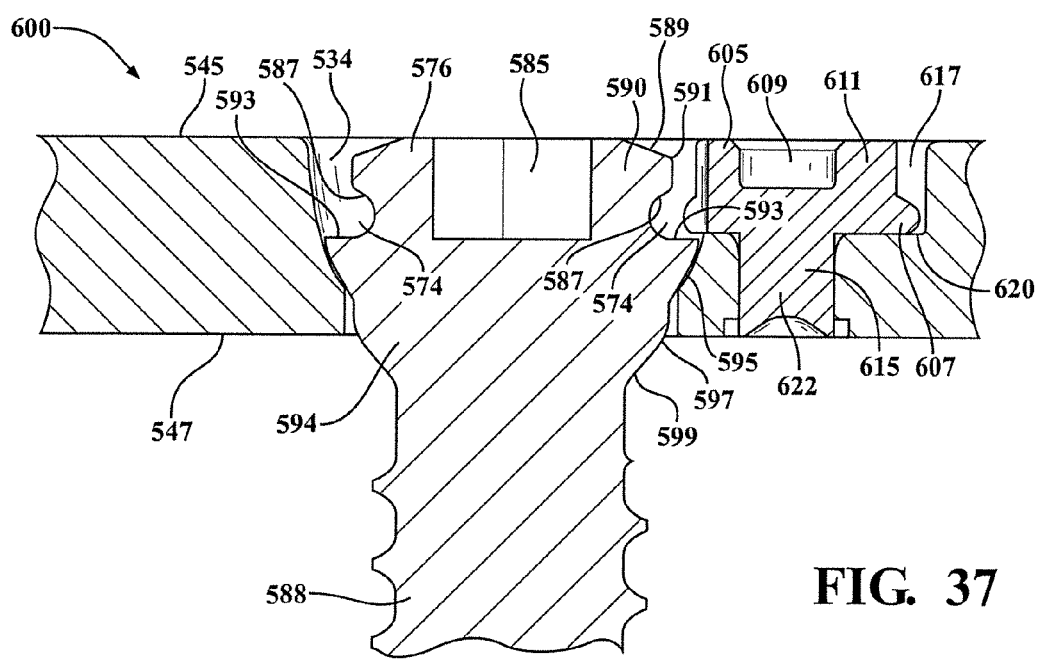
FIG. 37 illustrates a cross section view of the alternative screw locking mechanism of FIG. 36 taken from line 37.
Figure 38:
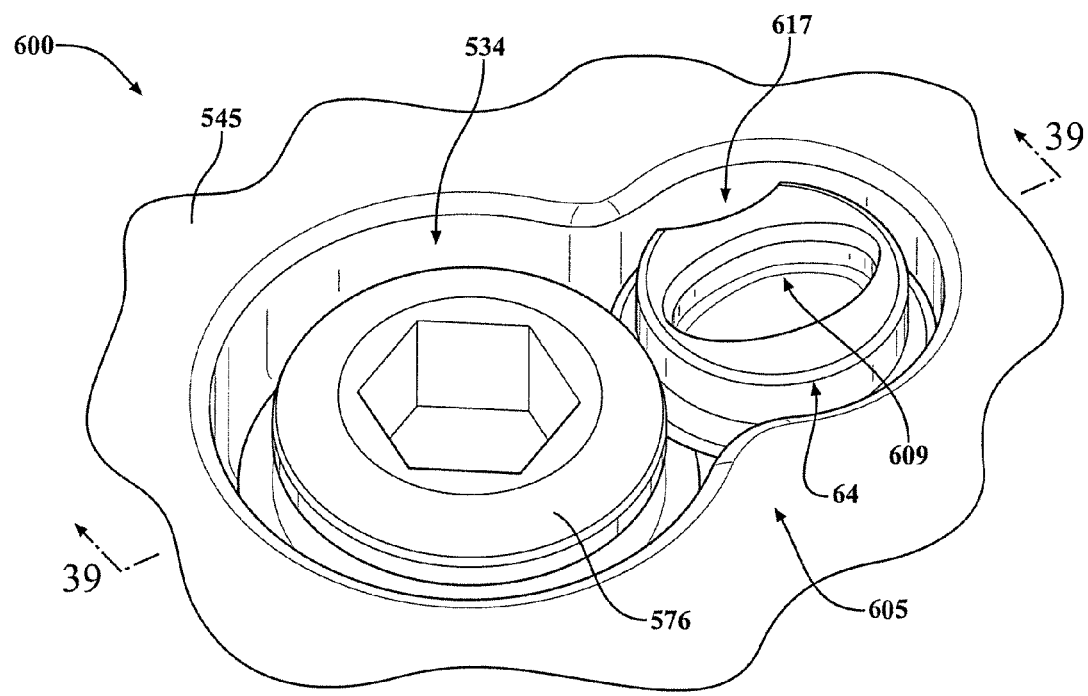
FIG. 38 illustrates a top environmental view of the alternative screw locking mechanism in a locked position.
Figure 39:
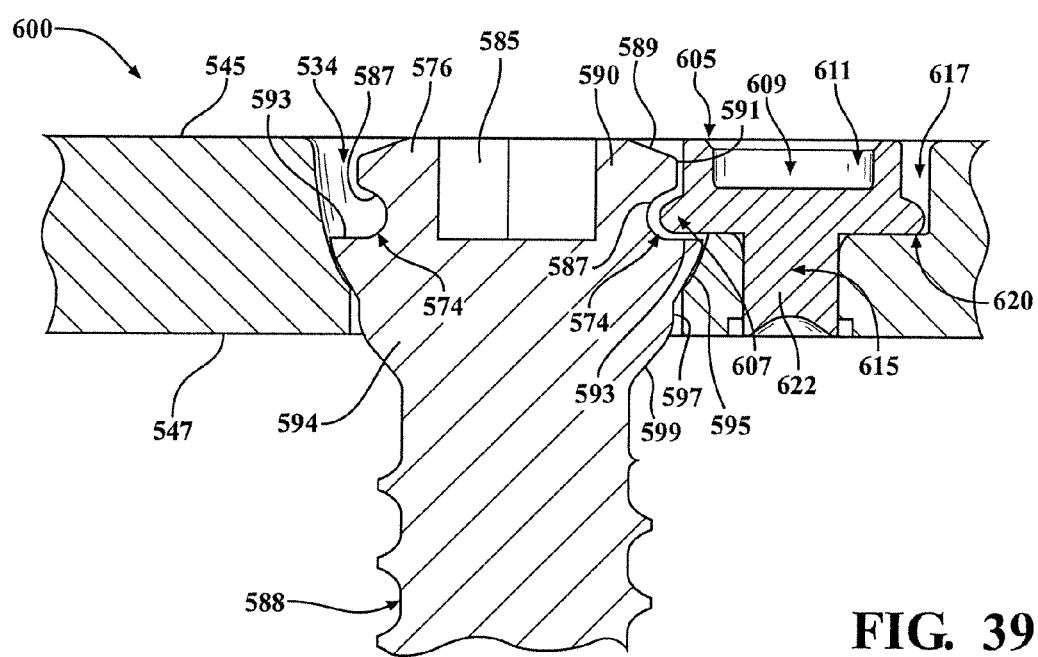
FIG. 39 illustrates a cross section view of the alternative screw locking mechanism of FIG. 38 taken from line 39.
Figure 40:
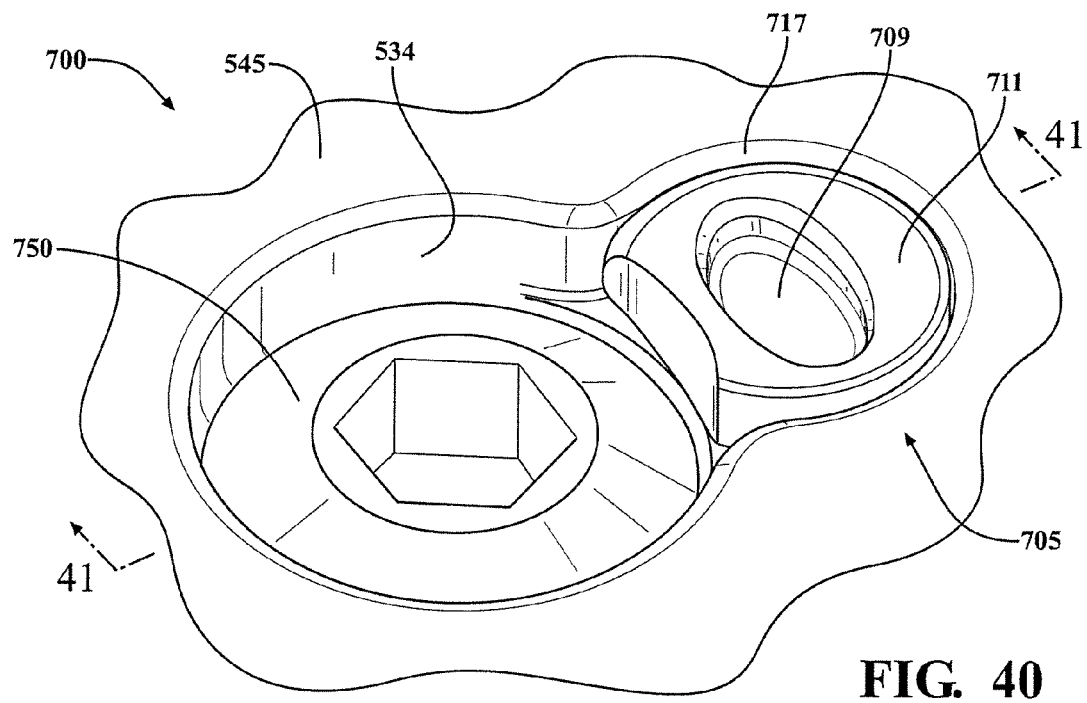
FIG. 40 illustrates a top environmental view of the second alternative screw locking mechanism in an unlocked position.
Figure 41:
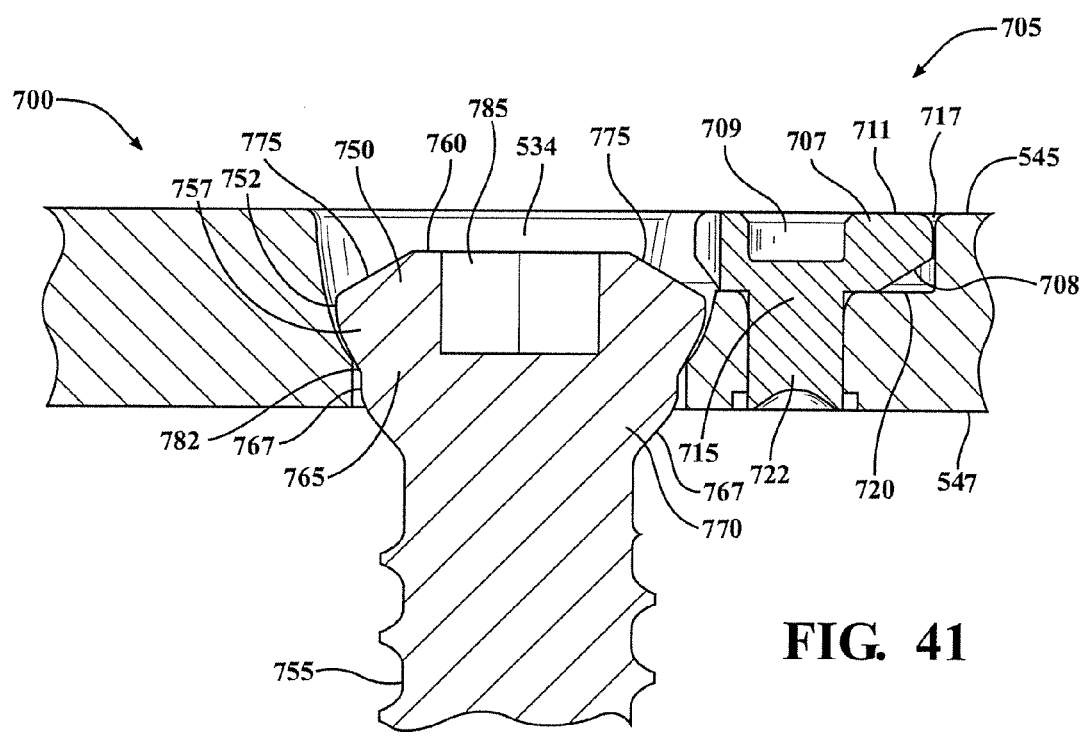
FIG. 41 illustrates a cross section view of the second alternative screw locking mechanism of FIG. 40 taken from line 41.
Figure 42:
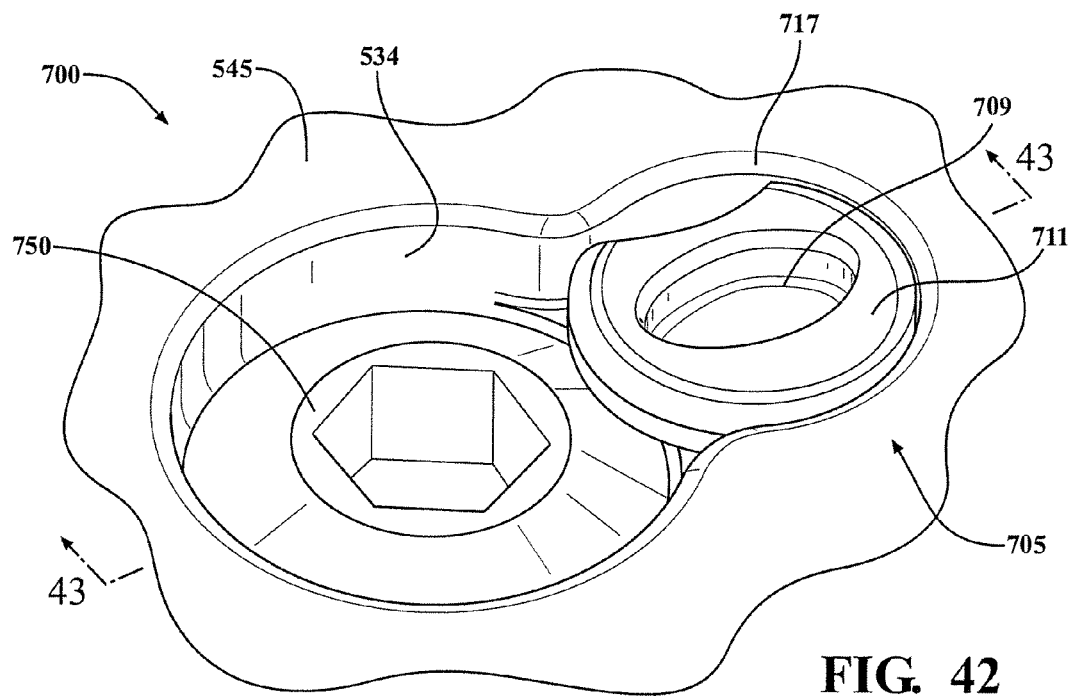
FIG. 42 illustrates a top environmental view of the second alternative screw locking mechanism in a locked position.

Now referring to FIGS. 33-35 the anatomical humeral fixation system 500 can also include a screw locking mechanism to prevent the screw from backing out. The axial screw locking assembly 568 having a hole 534 in the stem 530 having a horizontal retention groove 570, a frustoconical shaped split ring 572 and a bone screw 576 configured to interact with the split ring 572 as the bone screw 576 I inserted into the hole 534. The axial locking mechanism assembly 568 holds the bone screw 576 in place thus keeping the stem 530 secured to the bone. The horizontal retention groove 570 is located in the stem's 530 inner perimeter 582 of the hole 534, this allows the ring to expand 580 and be relaxed 572 as the bone screw 576 is inserted and seated through the hole 534. Furthermore, the bone screw 576 contains a retention groove 574 that is spherical and with a width that is larger than the size of the split ring 580. The outside diameter 584 of the split ring 570 fits the horizontal groove 570 of the inner perimeter 582 of the hole 534 of the stem 530 and the ring's 572 inside diameter 586 is configured to fit the bone screw 576 including the bone screw retention groove 574. Further, the groove 570 width and depth is larger than the split ring 580 to allow the ring 580 the freedom to move within the groove 570 so that the bone screw 576 may have the freedom of realignment. It should be appreciated that the split ring 572 is manufactured from medical grade material that is rigid enough to hold its shape but also resilient enough to allow the split ring 580 to contract and expand.

The bone screw 576, as illustrated in FIGS. 33-39, has a shaft 588 and a head 590. The head 590 is disposed above a top portion 592, the head 590 and top portion 592 being generally spherical. The bone screw 576 has a middle spherical portion 597 disposed between the top portion 592 and a bottom spherical portion 594. The bottom spherical portion 594 connected to the shaft 588. The screw 576 has a retention groove 574 configured to receive the split ring 580. The retention groove 574 is generally spherical and disposed in the top portion 592 of the screw 574. The retention groove 574 is similar in size to the split ring 580 so to lock in the split ring so that when the screw 576 realigns it still cannot back out. The retention groove 574 has an upper portion 587 and a lower portion 593, the lower portion 593 rounds out to a substantially flat bottom that protrudes axially beyond the upper portion 587 while maintaining its coaxial shape. The upper portion 587 extends radially into a substantially straight portion 591 until abutting the head portion 590 by transitioning axially into an angled portion 589. The upper portion 587 maintains its coaxial shape. The head portion 590 has an aperture 585 configured to receive a tool or other device to rotate or drive the bone screw 576. The middle spherical portion 597 flares out 595 and abuts the protrusion of the lower portion 593 while maintaining its spherical geometry. The bottom spherical portion abuts the shaft 588 at a lower end and flares 599 where it abuts the middle spherical section 597. The flared portions 595, 599 interact with the tapered inner perimeter 582 of the hole 534 so that the screw has the freedom to realign as necessary, up to five degrees. The shaft 588 has helix with a pitch, channel depth, and flight width that would be recognized by one skilled in the art for this type of application. The bone screw 576 material is a medical grade rigid material such as, without limitation, a composite or titanium material.

In FIGS. 36-39 an alternative screw locking mechanism is shown. The offset screw locking mechanism 600 has a rotating locking member 605 configured to interact with a retention groove 574 of a bone screw 576. The rotating locking member 605 is disposed in the stem 530 and is recessed in a circular depression 617 below the top surface 545. The depression 617 abuts the stem's 530 hole 534 for the bone screw 576. The rotating locking member 605 has a semi-arcuate shape with an aperture 609 on the upper surface portion 611 so to provide an access point to rotate the rotating locking member 605. At a lower surface portion 615 the rotating locking member 605 has a protrusion 607 that is configured to lock into the retention groove 574 of the bone screw 576. The protrusion 607 can only fit the retention groove 574 when the bone screw 576 is fully seated and the rotating locking member 605 is rotated into position. Further, the protrusion 607 is a narrower width and does not abut the back wall of the retention groove 574 so as to provide thereby allowing the screw 576 the freedom to realign as needed. The rotating locking member 605 rotates within the depression 617 by using a ledge 620 as a guide and a shaft 622 on the lower portion 615 of rotating locking member 605. The shaft 622 is disposed within the depression 617 and operatively coupled to the stem 530. The bone screw is configured to receive the rotating locking member 605. It should be appreciated that the rotating locking member 605 is manufactured from medical grade material that is rigid material, such as, without limitation, a composite, steel or titanium.

Now referring to FIGS. 40-43, a second alternative screw locking mechanism is shown. The offset screw locking mechanism 700 has a rotating locking member 705 configured to interact with an angle surface 775 on the head 760 of the bone screw 750. The rotating locking member 705 is disposed in the stem 530 and is recessed in a circular depression 717 below the top surface 545. The depression 717 abuts the stem's 530 hole 534 for the bone screw 576. The rotating locking member 705 has a semi-arcuate shape with an aperture 709 on the upper surface portion 711 so to provide an access point to rotate the rotating locking member 705. At a lower surface portion 715 rotating locking member 705 has a protrusion 707 that is angled 708 so to be configured to match the angled surface 775 of the bone screw 750. These two angles 708, 775 compliment each other locking the bone screw 750 into the stem 530 while still allowing the bone screw 750 to float due to a gap 725 between the angled surfaces 708, 775 and a gap between the bone screw 750 and the inner perimeter 582 of the hole 534. These gaps allow the bone screw 750 the freedom to realign as discussed earlier while still preventing the screw 750 from backing out. The protrusion angle 708 of the rotating locking member 705 can only fit the angled surface 775 of the bone screw 750 when the bone screw 750 is fully seated and the rotating locking member 705 is rotated into position. The rotating locking member 705 rotates within the depression 717 by using a ledge 720 as a guide and a shaft 722 operatively attached to the lower portion 715 of the rotating locking member 705. The shaft 722 is disposed within the depression 717 and operatively coupled to the stem 530. It should be appreciated that the rotating locking member 705 is manufactured from medical grade material that is rigid material, such as, without limitation, a composite, steel or titanium.

The bone screw 750 has a shaft 755 and a head 760. The head 760 is disposed above a top portion 751, the head 760 and top portion 751 being generally spherical. The bone screw has a middle spherical portion 765 disposed between the top portion 751 and a bottom spherical portion 770. The bottom spherical portion 770 connected to the shaft 755. The top portion 751 having an angled surface 775 configured to interact with and receive the rotating locking member 705. Further, the top portion 751 maintains its coaxial shape. The top portion 751 flares out 752 axially as this portion travels towards the angled surface 775 in the radial direction. The head portion 760 has an aperture 785 configured to receive a tool or other device to rotate or drive the bone screw 750. The middle spherical portion 765 flares out 767 while maintaining its spherical geometry. The bottom spherical portion 770 connects to the shaft 755. The flared portions 752, 767 interact with the tapered inner perimeter 582 of the hole 534 so that the screw 750 has the freedom to realign as necessary, up to five degrees. The shaft 755 has helix with a pitch, channel depth, and flight width that would be recognized by one skilled in the art for this type of application. Further, the bone screw is driven, screwed, drilled, or the like into the bone B at a depth sufficient to hold the screw 750 and the plate in place as would be apparent to one skilled in the art. The bone screw 750 material is a medical grade rigid material such as, without limitation, a composite or titanium material.

Figure 43:
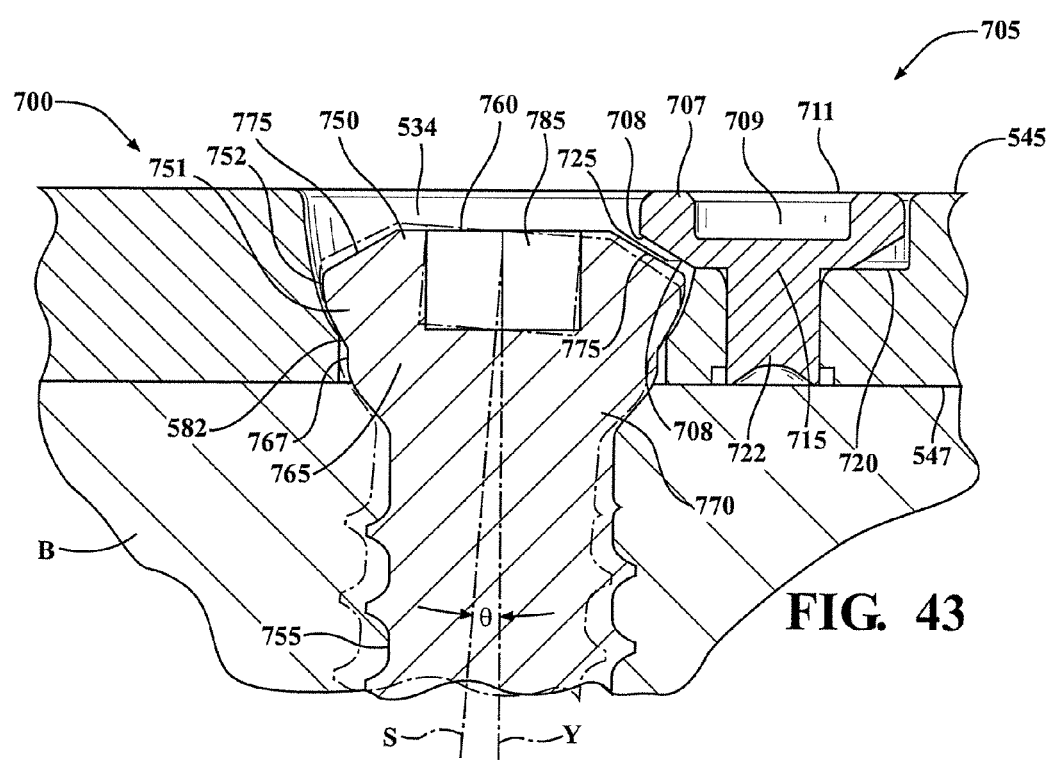
FIG. 43 illustrates a cross section view of the second alternative screw locking mechanism of FIG. 42 taken from line 43.

The bone screw angulation as illustrated in FIG. 43 and as discussed in the above arrangements and locking mechanism embodiments are shown as measured from the axis of the hole Y to the axis of the screw S. The angled difference φ as referenced from axis of the hole Y to the screw angulation axis S is between 2.5 and 5.0 degrees. This provides the freedom necessary for the bone screw 750 to realign itself during the bone's B healing process. It should be appreciated that the screw angulation S may be in any direction from the axis of the hole Y.

This detailed description provides examples including features and elements of the claims for the purpose of enabling a person having ordinary skill in the art to make and use the inventions recited in the claims. However, these examples are not intended to limit the scope of the claims, directly. Instead, the examples provide features and elements of the claims that, having been disclosed in these descriptions, claims and drawings, may be altered and combined in ways that are known in the art.

I claim:

1. An orthopedic repair implant assembly comprising:
   a bone screw;
   a base plate;
   the base plate having a top surface and a bottom surface, the base plate having a plurality of holes configured to receive the bone screw wherein the plurality of holes having an outer perimeter on the top surface and an inner perimeter extending through the base plate to the bottom surface such that the outer perimeter is larger in diameter at the top surface than the diameter of the inner perimeter at the bottom surface;
   a locking mechanism;
   the locking mechanism including a rotating locking member and the bone screw, the locking member disposed below the top surface of the base plate in a recessed circular depression so that the rotating locking member is flush with the top surface, the circular depression abuts the plurality of holes, the rotating locking member having a semi-arcuate shape that may be rotated over the bone screw into a locked position, the semi-arcuate shape having a protrusion, the protrusion having a surface extending at a complimentary angle that aligns with an angled surface of the bone screw when rotated to the locked position such that to retain the bone screw in the base plate, the surface of the protrusion being spaced apart from the angled surface of the bone screw to create a gap; and
   the bone screw having a shaft with a head at a first end thereof, the head being generally spherical, with a bottom spherical portion connected to the shaft and a top spherical portion having the angled surface, the angled surface configured to compliment the angle of the protrusion of the rotating locking member.

2. The orthopedic repair implant assembly of claim 1, wherein the gap between the surface of the protrusion and the angled surface of the bone screw provide for the bone screw to have an angulation between 2.5 degrees and 5.0 degrees measured from an axis of the hole to an axis of the bone screw.

3. An orthopedic repair implant assembly comprising:
   a bone screw;
   a base plate;
   the base plate having a top surface and a bottom surface, the base plate having a plurality of holes configured to receive the bone screw wherein the plurality of holes having an outer perimeter on the top surface and an inner perimeter extending through the base plate to the bottom surface such that the outer perimeter is larger in diameter at the top surface than the diameter of the inner perimeter at the bottom surface, and a horizontal grove in a upper portion of the inner perimeter configured for receiving a split ring;
   a locking mechanism;
   the locking mechanism including the horizontal groove in the upper portion of the inner perimeter plurality of holes, the bone screw and the split ring, the split ring having a generally frustoconical shape wherein the split ring has an inside diameter and an outside diameter, the outside diameter configured to fit within the horizontal groove of the plurality of holes, the inside diameter configured to fit the bone screw; and
   the bone screw comprising a shaft with a head at a first end thereof, the head being generally spherical, with a bottom spherical portion connected to the shaft and a top spherical portion having an annular groove configured to receive the split ring;
   wherein the split ring expands the inside and the outside diameters from a relaxed state around the bone screw during the installation and rotation of the bone screw, the split ring being removably seated in the annular groove when the bone screw is fully seated in the plurality of holes.

4. An orthopedic repair implant assembly comprising:
   a bone screw;
   a base plate;
   the base plate having a top surface and a bottom surface, the bottom surface is in contact with a bone surface, the base plate having a plurality of holes configured to receive the bone screw wherein the plurality of holes having an outer perimeter on the top surface and an inner perimeter extending through the stem to the bottom surface such that the outer perimeter is larger in diameter at the top surface than the diameter of the inner perimeter at the bottom surface;
   the top surface of the base plate having at least one suture locking member attached to a peg, the peg protruding from the top surface generally in the direction away from the bottom surface, the at least one suture locking member having a bore; and
   an elongated member can be inserted through the bore of the at least one suture locking member, once fully inserted, the bore can be compressed thereby locking the elongated member into the at least one suture locking member.

5. The orthopedic implant assembly of claim 4, wherein:
the plurality of holes having a locking mechanism, the locking mechanism having a horizontal groove in an upper portion of the inner perimeter plurality of holes, the bone screw, and a split ring, the split ring having a generally frustoconical shape wherein the split ring has an inside diameter and an outside diameter, the outside diameter configured to fit within the horizontal groove of the plurality of holes, the inside diameter configured to fit the bone screw; and
the bone screw comprising a shaft with a head at a first end thereof, the head being generally spherical, with a bottom spherical portion connected to the shaft and a top spherical portion having an annular groove configured to receive the split ring;
wherein the split ring expands the inside and outside diameters from a relaxed state around the bone screw during the installation and rotation of the bone screw, the split ring being removably seated in the retention groove when the bone screw is fully seated in the plurality of holes.

6. The orthopedic repair implant assembly of claim 4, wherein the bore is angled relative to the top surface of the base plate.

7. The orthopedic repair implant assembly of claim 4, wherein the plurality of holes having a locking mechanism, the locking mechanism including a rotating locking member and the bone screw, the rotating locking member disposed below the top surface of the base plate in a recessed circular depression so that the rotating locking member is flush with the top surface, the circular depression abuts the plurality of holes, the rotating locking member having a semi-arcuate shape that may be rotated over the bone screw into a locked position, the semi-arcuate shape having a protrusion, the protrusion having a surface extending at a complimentary angle that aligns with an angled surface of the bone screw when rotated to the locked position such that to retain the bone screw in the base plate, the surface of the protrusion being spaced apart from the angled surface of the bone screw to create a gap; and
the bone screw having a shaft with a head at a first end thereof, the head being generally spherical, with a bottom spherical portion connected to the shaft and a top spherical portion having the angled surface, the angled surface configured to compliment the angle of the protrusion of the rotating locking member.

8. The orthopedic repair implant assembly of claim 4, wherein the plurality of holes having a locking mechanism, the locking mechanism including a rotating locking member and the bone screw, the rotating locking member having a protrusion disposed below the top surface of the base plate in a recessed circular depression so that the rotating locking member is flush with the top surface of the base plate, the circular depression abuts the plurality of holes, the rotating locking member having a semi-arcuate shape that may be rotated into an annular groove disposed on an upper portion of a head of the bone screw, the annular groove configured to accept a protrusion from the rotating locking member; and
the bone screw having a shaft with a head at a first end thereof, the head being generally spherical, with a bottom spherical portion connected to the shaft and a top spherical portion having the annular groove, the annular groove configured to compliment the protrusion of the rotating locking member.

* * * * *